(12) United States Patent
Wang et al.

(10) Patent No.: US 11,672,440 B2
(45) Date of Patent: Jun. 13, 2023

(54) LOW COST DIABETES BREATH ANALYZER BASED ON NANOSTRUCTURED $K_2W_7O_{22}$ MATERIAL

(71) Applicant: NDSU Research Foundation, Fargo, ND (US)

(72) Inventors: Danling Wang, Fargo, ND (US); Qifeng Zhang, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 763 days.

(21) Appl. No.: 16/562,104

(22) Filed: Sep. 5, 2019

(65) Prior Publication Data

US 2020/0077923 A1   Mar. 12, 2020

Related U.S. Application Data

(60) Provisional application No. 62/727,843, filed on Sep. 6, 2018.

(51) Int. Cl.
| | |
|---|---|
| *A61B 5/08* | (2006.01) |
| *G01N 33/497* | (2006.01) |
| *G01N 27/12* | (2006.01) |
| *A61B 5/00* | (2006.01) |
| *A61B 90/00* | (2016.01) |

(52) U.S. Cl.
CPC ........... *A61B 5/082* (2013.01); *A61B 5/4836* (2013.01); *A61B 5/7282* (2013.01); *G01N 27/127* (2013.01); *G01N 33/497* (2013.01); *A61B 2090/064* (2016.02); *A61B 2562/0285* (2013.01)

(58) Field of Classification Search
CPC ............. A61B 5/082; A61B 2090/064; A61B 2562/0285; G01N 27/127; G01N 33/497
See application file for complete search history.

(56) References Cited

U.S. PATENT DOCUMENTS

| | | | |
|---|---|---|---|
| 7,003,337 B2 | 2/2006 | Harjunmaa et al. | |
| 2007/0048180 A1* | 3/2007 | Gabriel | G01N 33/497 |
| | | | 422/400 |
| 2009/0275852 A1* | 11/2009 | Oki | G01N 33/497 |
| | | | 600/532 |

OTHER PUBLICATIONS

Sitthisuntorn Supothina, Mantana Suwan, Anurat Wisitsoraat, Hydrothermal synthesis of K2W4O13 nanowire with high H2S gas sensitivity, Microelectronic Engineering, vol. 126, pp. 88-92 (Year: 2014).*

Q. Zhang and D. Wang, "Room temperature acetone sensor based on nanostructured K2W7O22," 2016 IEEE Sensors, 2016, pp. 1-3, doi: 10.1109/ICSENS.2016.7808635. (Year: 2016).*

(Continued)

*Primary Examiner* — Jennifer Wecker
*Assistant Examiner* — Alea N. Martin
(74) *Attorney, Agent, or Firm* — Stites & Harbison, PLLC; Mandy Wilson Decker; Gary N. Stewart

(57) ABSTRACT

Disclosed herein is a device detecting volatile organic compounds, such as acetone, using nanostructured $K_2W_7O_{22}$ crystals. Methods for detecting a subject in a state of ketosis, such as diabetes, using a volatile organic sensing device are disclosed. A method for synthesizing $K_2W_7O_{22}$ nanostructured sensing crystals is further disclosed.

12 Claims, 22 Drawing Sheets

(56) References Cited

OTHER PUBLICATIONS

International Diabetes Federation (IDF), Diabetes Atlas third Ed., Brussels, 2006.

National Diabetes Statistics Report, 2017. Available: https://www.cdc.gov/diabetes/pdfs/data/statistics/national-diabetes-statistics-report.pdf.

Qiao, Y., et al. (May 2014). Breath Ketone Testing: A New Biomarker for Diagnosis and Therapeutic Monitoring of Diabetic Ketosis. BioMed. Research International, [Online], 2014(2014), pp. 1-5. Available: https://www.hindawi.com/journals/bmri/2014/869186/.

March, W.F., et al. "Clinical trial of a noninvasive contact lens glucose sensor," Diabetes Technology & Therapeutics, 2004, pp. 782-789.

Johannessen, A.E., et al. "Injectable Osmotic Glucose Sensor and the Development of a Nanoporous Semi-permeable Membrane." Diabetes Technology Meeting, 2005, San Francisco: Diabetes Technology Society.

Brown, H.T., et al. "Clinical assessment of near infrared spectroscopy for noninvasive diabetes screening." Diabetes Technology & Therapeutics, 2005, pp. 456-466.

Pandey, R., et al. (Jan. 2017). Noninvasive Measurements of Blood Glucose with Raman Spectroscopy. Accounts ot Chemical Research. [Online] 50(2), pp. 2564-272, 2017. Available: http://pubs.acs.org/doi/ipdf/10.1021/acs.accounts.6b004726.

Cygnus Inc.(Aug. 2002). Glucowatch G2: Automatic Glucose Biographer and Auto-sensors. Redwood City, CA. [Online]. Available: https://www.accessdata.fda.gov/cdrh_docs/pdf/P990026S008b.pdf.

Novak, B.J. "Non-invasive monitoring of metabolism, diabetes and oxidative stress using exhaled human breath." Ph D. dissertation, Dept. Chem., Univ. of California, Irvine, 2007.

Miekisch, W., et al. (Sep. 2004). Diagnostic potential of breath analysis—focus on volatile organic compounds. Clinica Chimica Acta. [Online]. 347(1-2), pp. 25-39. Available:http://www.sciencedirect.com/science/article/pii/S0009898104002256.

Amann, A., et al. (Feb. 2007).Breath analysis: the approach towards clinical applications. Mini-reviews in medicinal chemistry, 7(2), pp. 115-129.

Shirasu, M., et al. (Sep. 2011). The scent of disease: volatile organic compounds of the human body related to disease and disorder. Journal of biochemistry.[Online]. 150(3), pp. 257-266. Available: https://academic.oup.com/jb/article/150/3/257/867730/The-scent-of-disease-volatile-organic-compounds-of.

Pennazza, G., et al. "Interpretation of exhaled volatile organic compounds," European respiratory monograph exhaled biomarkers, 49, ERS., UK, 2010, pp. 115-129.

Wang, C., et al. (Jan. 2010).A study on breath acetone in diabetic patients using a cavity ringdown breath analyzer Exploring correlations of breath actone with blood glucose and glycohemoglobinale. IEEE Sensors Journal, [Online], 10(1), pp. 54-63. Available : http://ieeexplore.ieee.org/stamp/stamp.jsp?arnumber=5350908.

Deng, C., et al. (Oct. 2004). Determination of acetone in human breath by gas chromatography—mass spectrometry and solid-phase microextraction with on-fiber derivatization. Journal of Chromatography B, [Online], 810(2), pp. 269-275. Available: http://www.sciencedirect.com/science/article/pii/S15700232040065792via%3Dihub.

Yoshimura, M., et al. (Apr. 2008). Hydrothermal processing of materials: past, present and future. J. Mater. Sci., [Online] 43(7), pp. 2085-2103. Available: https://link.springer.com/article/10.1007/s10853-007-1853-x.

Jitputti, J., et al. (Jan. 2008). Synthesis of TiO2 nanotubes and its photocatalytic activity for H2 evolution. Japanese Journal of Applied Physics, [Online], 47(1), pp. 751-756. Available: http://iopscience.iop.org/article/10.1143/JJAP.47.751/pdf.

Supothina, S., et al. (Aug. 2014). Hydrothermal synthesis of K2W4O13 nanowire with high H2S gas sensivitity. Microelectronic Engineering. [Online]. 126, pp. 88-92. Available: http://www.sciencedirect.com/science/article/pii/S0167931714002676.

Wang, D., et al. "Room temperature acetone sensor based on nanostructured K2W7O22." Sensors, 2016 IEEE, 2016, [Online], pp. 1-3. Available: http://ieeexplore.ieee.org/document/7808635/.

Hossain, M.R., et al. (Oct. 2017). Investigation of humidity cross-interference effect on acetone breath sensor based on nanostructured K2W7O22. Engineering Press, [Online], 1(1), pp. 30-34. Available: http://onlinepublishingpress.com/engineering-press/article-in-press.php.

Deng, C.H., et al. (Oct. 2004). Determination of acetone in human breath by gas chromatography-mass spectrometry and solid-phase microextraction with on-fiber derivatization. Journal of Chromatography B,[Online], 810(2), pp. 269-275.Available:http://www.sciencedirect.com/science/article/pii/S1570023204006579.

Sun, M.X., et al. (Feb. 2015). Determination of breath acetone in 149 Type 2 diabetic patients using a ringdown breath-acetone analyzer. Analytical and Bioanalytical Chemistry,[Online] 407(6), pp. 1641-1650. Available:https://link.springer.com/article/10.1007%2Fs00216-014-8401-8.

Righettoni, M., et al. (May 2010). Si:WO3 Sensors for Highly Selective Detection of Acetone for Easy Diagnosis of Diabetes by Breath Analysis. Analytical Chemistry, [Online], 82(9), pp. 3581-3587. Available :http://pubs.acs.org/doi/pdf/10.1021/ac902695n.

Righettoni, M., et al. (Aug. 2012). Breath acetone monitoring by portable Si: WO3 gas sensors. Analytica chimica acta, [Online] 738, pp. 69-75. Available: http://www.sciencedirect.com/science/article/pii/S0003267012008276?via%3Dihub.

Kao, K.W., et al. (May 2012). A Sub-ppm Acetone Gas Sensor for Diabetes Detection Using 10 nm Thick Ultrathin InN FETs. Sensors, [Online], 12(6), pp. 7157-7168. Available: http://www.mdpi.com/1424-8220/12/6/7157/htm.

Wang, L., et al. (Jul. 2008). Ferroelectric WO3 nanoparticles for acetone selective detection. Chemistry of Materials, [Online], 20(15), pp. 4794-4796. Available: http://pubs.acs.org/doi/pdfplus/10.1021/cm800761e.

Wang, L., et al. (Oct. 2010). Nanosensor Device for Breath Acetone Detection. Sensor Letters, [Online], 8(1-4), pp. 709-712. Available: http://www.ece.sunysb.edu/~milutin/pubs/journal/gasSensorSL10.pdf.

Vomiero, A., et al. (Dec. 2007). Controlled growth and sensing properties of In2O3 nanowires. Crystal Growth & Design. [Online]. 7(12), pp. 2500-2504. Available : http://pubs.acs.org/doi/pdf/10.1021/cg070209p.

Kakati, N., et al. (Oct. 2010). Thickness dependency of sol-gel derived ZnO thin films on gas sensing behaviors. Thin Solid Films, [Online] ,519(1), pp. 494-498. Available: http://www.sciencedirect.com/science/article/pii/S0040609010011193.

Murade, P.A., et al. (May 2011). Acetone gas-sensing performance of Sr-doped nanostructured LaFeO3 semiconductor prepared by citrate sol-gel route. Current Applied Physics, [Online], 11(3), pp. 451-456. Available: http://www.sciencedirect.com/science/article/pii/S1567173910002749.

Teleki, A., et al. (Dec. 2006). Sensing of organic vapors by flame-made TiO2 nanoparticles. Sensors and Actuators B-Chemical, [Online], 119(2), pp. 683-690. Available: http://www.sciencedirect.com/science/article/pii/S0925400506000475.

Qu, F., et al. (Aug. 2014). Hierarchical Fe3O4@Co3O4 core-shell microspheres: Preparation and acetone sensing properties. Sensors and Actuators B-Chemical, [Online], 199,pp. 346-353. Available: http://www.sciencedirect.com/science/article/pii/S0925400514004031.

Ahn, H., et al. (Aug. 2011). Enhanced UV activation of electrochemically doped Ni in ZnO nanorods for room temperature acetone sensing. Chemical Physics Letters,[Online], 511(4-6), pp. 331-335. Available: http://www.sciencedirect.com/science/article/pii/S000926141100755X.

Rydosz, A. A Negative Correlation Between Blood Glucose and Acetone Measured in Healthy and Type 1 Diabetes Miellitus Patient Breath, J Diabetes Sci Technol 2015, 9, 881-884, doi: 10.1177/1932296815572366.

Jamalabadi, H., et al. IEEE Sens. J., 2017, 17, 2322-2328.

Kao, K.W.. et al. Sensors, 2012, 12, 7157-7168.

(56) References Cited

OTHER PUBLICATIONS

Hazra, A., et al. Presented in Seventh International Conference on Sensing Technology (ICST), IEEE, Wellington, New Zealand, Dec. 3-5, 2013.

Subhashis, D., et al. IEEE-EDL, 2017, 38, 383-386.

Chemiresistors,http://www.sandia.gov/mstc/_assets/documents/Fact_Sheets/sensors/2chemiresistor.pdf,(accessed Apr. 7, 2018).

Wang, D., et al. IEEE Sens. J., 2018, 18, 4399-4404.

Barsan. N., et al. J. of Electroc., 2001, 7, 143-167.

Dipole moment, https://en.wikipedia.org/wiki/Dipole_moment (Apr. 3, 2018).

Caveman, B. (Mar. 2014). Ketonix Review. [Online]. Available: bjjcaveman.com/2014/03/15/ketonix-review/.

Soper, T. (Nov. 2013).This handheld device helps you lose weight by detecting acetone levels in your breath. [Online]. Available: www.geekwire.com/2013/small-device-detects-acetone-levels-breath-measure-fat-burning/.

Newton, C.A., et al. Arch Intern Med., 2004, 164: 1925-1931.

Anderson. J.C. Obesity, 2015, 23: 2327-2334.

McGuire, L.C. , et al. Emerg. Med. J. 2006, 23:417-420.

Electrostatic Interactions. Available online: https://www.sciencedirect.com/topics/chemistry/electrostaticinteractions (accessed on Sep. 1, 2018).

Fine, G.F., et al. Metal Oxide Semi-Conductor Gas Sensors in Environmental Monitoring. Sensors 2010, 10, 5469-5502. [CrossRef] [PubMed].

Chemical Sensors. Available online: https://www.nap.edu/read/4782/chapter/10#74 (accessed on Oct. 15, 2018).

Sensor. Available online: https://en.wikipedia.org/wiki/Sensor (accessed on Oct. 15, 2018).

Kargar, A. Sensitivity Analysis of Silicon Nanowire Chemical Sensor. In Proceedings of the 8th IEEE Conference on Nanotechnology, Arlington, TX, USA, Aug. 18-21, 2008.

Hossain, M.R., et al. (2018) Highly Sensitive Room-Temperature Sensor Based on Nanostructured K2W7O22 for Application in the Non-Invasive Diagnosis of Diabetes. Sensors 18(11): 3703-3712.

Buszewski, B., et al. (2007). Human exhaled air analytics: Biomarkers of diseases. Biomedical Chromatography, 21 (6), 553-566. doi:10.1002/bmc.835.

Konvalina, G., et al. (2014). Sensors for Breath Testing: From Nanomaterials to Comprehensive Disease Detection. Accounts of Chemical Research, 47(1), 66-76. doi:10.1021/ar400070m.

Jia, Q Q., et al. (2014). Exposed facets induced enhanced acetone selective sensing property of nanostructured tungsten oxide. Journal of Materials Chemistry A, 2(33), 13602-13611. doi:10.1039/c4ta01930j.

Tang, B. L., et al. (2015). First-Principles Study on Hexagonal WO3 for HCHO Gas Sensing Application. Acta Metallurgica Sinica-English Letters, 28(6), 772-780. doi:10.1007/S40195-015-0260-6.

Woodward, P.M., et al. (1997). Ferroelectric tungsten trioxide. Journal of Solid State Chemistry, 131(1), 9-17. doi:10.1006/jssc.1997.7268.

Arai, M., et al. (1990). Raman Studies of Phase-Transitions in Gas-Evaporated WO3 Microcrystals. Solid State Communications, 75(7), 613-616. doi:10.1016/0038-1098(90)90429-f.

Lopes, L.F., et al. (2018). Silver-controlled evolution of morphological, structural, and optical properties of three dimensional hierarchical WO3 structures synthesized from hydrothermal method. Journal of Alloys and Compounds, 736, 143-151. doi:10.1016/j.jallcom.2017.11.095.

Li, T.T., et al. (2018). Xanthate sensing properties of Pt-functionalized WO3 microspheres synthesized by one-pot hydrothermal method. Ceramics International, 44(5), 4814-4823. doi:10.1016/j.ceramint.2017.12.069.

Miu, W.J., et al. (2015). Guanidine sulfate assisted synthesis of hexagonal WO3 nanoparticles with enhanced adsorption properties. Dalton Transactions, 44(16), 7419-7427.

\* cited by examiner

LOW COST DIABETES BREATH ANALYZER BASED ON NANOSTRUCTURED $K_2W_7O_{22}$ MATERIAL

RELATED APPLICATIONS

This application claims priority from U.S. Provisional Patent Application No. 62/727,843 filed on Sep. 6, 2018, the entire disclosure of which is incorporated herein by this reference.

TECHNICAL FIELD

The present invention relates to devices and methods for detection and diagnosis of Diabetes using measurements from exhaled breath.

BACKGROUND AND SUMMARY

The diagnosis of diseases at an early stage can allow to improved treatment outcomes. For some chronic diseases, there is also a need for convenient ways to monitor the disease progression and/or status. Diabetes, as one of the most rapidly-growing chronic diseases in the world, results in a number of serious medical complications such as blindness, renal failure, and heart disease, and has become a great threat to human health. [1, 2] Since this disease is caused by metabolic disorders featured with high blood glucose, for patients with diabetes, it is critically important to monitor and keep blood sugar under control, in order to reduce risk of complications. Blood and urine tests have been two of the most common methods used to diagnosis and monitor diabetes.

A blood test to diagnose diabetes is generally an accurate method. However it often needs to be conducted in a hospital or clinic by a specialist, and relies on special instruments. Accordingly, such blood tests are often inconvenient and have a relatively high cost. Moreover, a blood test is invasive, requiring the skin to be ruptured in order to extract a drop of blood needed for a glucose test. As such, such blood tests can also be painful and carry a risk if infection if not properly conducted.

Alternatively, a urine test is a non-invasive way to diagnose and monitor diseases. However, the urine test cannot be done anywhere and anytime, i.e., it is still inconvenient. Also, urine measurements are less reliable than blood measurements and are not used to diagnose diseases or evaluate treatment for disease. [3]

Therefore, there is a need of a non-invasive, accurate, convenient, and inexpensive test that can be used at home for disease diagnosis and monitoring on daily basis.

As compared to the other existing noninvasive methods for diabetes diagnosis [4-9], a breath sample containing the biomarker from a subject is an excellent candidate because breath is abundant, and collecting a breath sample is non-invasive and convenient. [10] The development of breath analyzers as a new sensing technology has been emerging in the past two decades for disease diagnosis and monitoring. A breath analyzer and/or method for use in the context of diabetes would addresses all of the issues mentioned above as a simple, repeatable, reliable, and convenient method for patients themselves to perform long-term clinical monitoring.

Breath can be used as a way of disease diagnosis because of volatile-organic-compounds (VOCs), which are gaseous chemicals found in human breath. VOCs are formed from different metabolic processes and specific VOCs have been linked to certain diseases, called biomarkers, due to how they can alter these processes. [55] After a VOC has been linked to a specific condition, it can be utilized to perform rapid and non-invasive methods for screening and diagnosing the linked disease. [56] Among other VOCs found in human breath, acetone has been identified to correlate with blood-glucose levels and can be used as a biomarker for diabetes.[55] Patients with diabetes are unable to effectively use (type II) or make insulin (type I). Their body will begin to burn fat instead of glucose, generating acetone, which is expelled through human breath.[55] Noninvasive methods for detection of VOCs have been developed using methods such as gas chromatography-mass spectrometry and solid-phase microextraction. These types of techniques are very precise and can reach a low detection limit of 0.049 ppb acetone. [16] However, those techniques require large machines, which are bulky and need highly trained personnel to operate effectively. Compared to these methods, a breath-analyzer based on solid-state nanomaterials can provide a simple, light-weight, reliable, and convenient method for disease diagnosis and health-status monitoring.

The threshold of acetone concentration in human breath to distinguish healthy person and pre-diabetics is only around 0.76 ppm. The diagnosis of diabetes can be determined based on concentration of breath acetone higher than 1.71 ppm. [16] Therefore, to diagnose and prevent diabetes at an early stage, a suitable device is needed that can detect acetone to the low concentration of 0.76 ppm. However, it is quite challenging to accurately detect breath acetone not only due to the low concentration of only about 0.76 ppm or even less, but also because of the added complexity of human breath. In addition, the relative humidity in exhaled human breath is quite high, about 90%, which also makes acetone detection more difficult. So, it is needed to develop an acetone sensor with high sensitivity, as well as good selectivity and stability to overcome these challenges.

TABLE I

THE EXISTING MATERIALS AND SENSORS FOR ACETONE DETECTION

| Sensing Material | Lowest detection limit | Operation temperature, condition, and carrying gas | Mechanism |
|---|---|---|---|
| InN epitaxial thin film | 0.4 ppm | 200° C. | Uses a furnace, and Au electrode. | M-1[1] |
| Cr-doped $WO_3$ nanoparticles | 0.2 ppm | 400° C.[27] | Uses Pt electrode and micro heater.[28] | M-1[1] |
| Si-doped $WO_3$ nanoparticles | 20 ppb | 350-400° C. | Uses a tubular furnace[24] or Pt heater and Pt electrode.[25] | M-1[1] |

TABLE I-continued

THE EXISTING MATERIALS AND SENSORS FOR ACETONE DETECTION

| Sensing Material | Lowest detection limit | Operation temperature, condition, and carrying gas | | Mechanism |
|---|---|---|---|---|
| $In_2O_3$ nanowires | 25 ppm | 400° C. | Uses Pt electrode and heater.[29] | M-1[1)] |
| ZnO nanoparticles | 100 ppm | 200° C. | Uses Ru electrode and $RuO_2$ heater.[30] | M-1[1)] |
| $La_{0.7}Sr_{0.3}FeO_3$ nanoparticles | 200 ppm | 275° C. | Use Au electrode and Pt wires.[31] | M-2[1)] |
| $TiO_2$ nanoparticles | 1 ppm | 500° C. | Uses a furnace, and Au wires.[32] | M-2[1),2)] |
| $Fe_3O_4@Co_3O_4$ core-shell microspheres | 20 ppm | 160° C. | Uses Au electrode and Pt wires.[33] | M-2[1)] |
| Ni-doped ZnO nanorods + UV irradiation | 100 ppm | Room temperature | | M-3[1)] [34] |
| $K_2W_7O_{22}$ nanorods | 2.0 ppm | Room temperature | | M-3[1)] |

Notes:
[1)]M-1: Redox reaction between acetone and oxygen adsorbed on n-type sensor material taking place at high temperature. Exposure to acetone leads to a decrease in the resistance of sensing film.
M-2: Redox reaction between acetone and oxygen adsorbed on p-type sensor material taking place at high temperature. Exposure to acetone leads to an increase in the resistance of sensing film.
M-3: Charge transfer between acetone molecules and p-type sensor material taking place at room temperature. Exposure to acetone leads to an increase in the resistance of sensing film.
[2)]p-type originates from $TiO_2$, transferring from anatase to rutile at 500° C.

Disclosed herein is a breath analyzer and methods for use in detecting volatile organic compounds (VOCs) in exhaled breath. This is based on the fact that the composition of exhaled breath (VOCs) of a patient is different from that of a healthy person due to the difference in cellular metabolic processes. [11-13] For example, it has been revealed that, for patients with lung cancer, the level of methyl hydrazine is higher than that of control individuals. [14] Acetone, has also received attention, because it exists in exhaled breath and can be used as a biomarker for diabetes due to a good correlation between the concentration of acetone in exhaled breath and blood sugar level in diabetics. [15, 16] This makes it possible to design a sensor device, which diagnoses diabetes by means of detecting the acetone concentration in human breath.

As disclosed herein, a breath analyzer based on a chemiresistive mechanism of a semiconductor makes use of a unique material, nanostructured $K_2W_7O_{22}$. Related methods are also disclosed. The analyzer includes a sensing film made by $K_2W_7O_{22}$ and the resistance of the sensing film can change upon the adsorption of acetone in the breath.

Since the material has been chosen to be significantly sensitive to acetone, the resistance change of the sensing film is proportional to the concentration of the target compound and can be adapted to reflect the level of certain acetone in the breath. The primary results have shown that the structure of as-synthesized $K_2W_7O_{22}$ is nanorod and it can sensitively detect acetone at room temperature. The sensing mechanism of $K_2W_7O_{22}$ to detect acetone was studied and it was found that not only high surface to area ratio featured by nanorod structures in $K_2W_7O_{22}$ provides large surfaceinteraction area but also the newly synthesized $K_2W_7O_{22}$ has a strong ferroelectric property at room temperature. This makes it capable of attracting high-dipole acetone molecules strongly and allows a highly efficient charge transfer process between the $K_2W_7O_{22}$ and acetone molecules. This study brings new insights into a breath analyzer for diabetes based on $K_2W_7O_{22}$ as an effective method to monitor the health.

As a biomarker, the concentration of acetone in breath is an important parameter to diagnose or monitor diabetes through use of a breath analyzer. Research finds that the concentration of acetone in breath is below 0.8 ppm for healthy people but above 1.7 ppm is for the patients with diabetes. [22] (In some literature, the thresholds are given as 1.0 ppm and 1.5 ppm for healthy and diabetic individuals, respectively. [23])

Many efforts have been made over the past decade to detect acetone with chemiresistive sensors. Table 1 listed the major materials reported in literature for acetone detection, and summarizes the lowest detection limit, operating temperature, and response mechanism of the corresponding sensors. It can be seen that (1) the lowest detection limit (or sensitivity) of the sensor device is very dependent on the sensing material, and (2) except for one paper reporting the use of Ni-doped ZnO for the detection of acetone operating at room temperature but showing a poor sensitivity (i.e., high detection limit, 100 ppm), most of the reported acetone sensors operate at high temperatures up to 500° C. Among these materials/sensors, Si-doped $WO_3$ has presented the most outstanding performance with the lowest detection limit reaching 20 ppb. It has been demonstrated that the high sensitivity of Si-doped $WO_3$ is due to the ferroelectric property of this material, [24-26] which makes it capable of interacting with acetone molecules very strongly, in view of a large dipole moment of acetone molecules ($\mu$=2.88 D).

Generally, in exhaled breath the acetone concentration is usually in the range of 0.3-0.8 ppm for healthy humans and above 1.7 ppm for diabetic patients [22, 35]. Therefore, the material should have detection limit as low as 0.8 ppm. As shown in Table 2, it describes the sensing performance based on five different structured sensors for acetone detection.

Among the five materials, the detection limits of PPy-WO$_3$ (20%), Pt—InN and K$_2$W$_7$O$_{22}$, are 0.37 ppm, 0.4 ppm, and 0.1 ppm respectively. The PPy-WO$_3$ (20%) material-based sensor has the lowest detection limit of 0.37 ppm. However, its sensitivity is very small, about 3.34×10$^{-3}$% with concentrations of acetone from 19 ppm to 316 ppm. So, the PPy-WO$_3$ (20%) material would not be an effective choice for breath acetone detection due to such poor sensitivity. The Ni/InGaN/GaN based Hetero structure sensor (7.6 & 2 sec) shows a faster response and recovery time at 100 ppm of acetone as compared to Pd/TiO$_2$/p-Si MIS sensor (16 & 30 sec). However, a lowest detection limit of 100 ppm is far too high to detect the threshold of acetone, 1.8 ppm. The MIS sensor can get the detection limit down to 10 ppm but still too high to be used for the detection of breath acetone in diabetics. Due to these limitations, these two sensors cannot be good option for breath acetone detection in diabetes diagnosis and monitoring. So far, only Pt—InN and KWO (K$_2$W$_7$O$_{22}$) do have the capability of detecting concentration of acetone less than 1.0 ppm with relative good sensitivity (recently results indicate that the lowest detection limit of KWO to acetone can be down to 0.1 ppm).

TABLE 3

A COMPARISON OF THE ELECTRIC DIPOLE MOMENT OF ACETONE WITH THOSE OF OTHER COMPOUNDS MOST COMMONLY PRESENT IN HUMAN BREATH

| Compound | Dipole Moment (Debye) |
| --- | --- |
| Acetone | 2.88 |
| Ethanol | 1.69 |
| Methanol | 1.70 |
| NO$_2$ | 0.316 |
| NO | 0.159 |
| NH$_3$ | 1.471 |
| CO$_2$ | 0 |
| CO | 0.112 |
| Ethane | 0 |
| Isoprene | 0.25 |
| Isopentane | 0.105 |
| H$_2$O | 1.855 |

Table 3 compares the dipole moments of acetone and other compounds commonly present in exhaled breath [43], clearly demonstrating that the dipole moment of acetone molecules is significantly larger than those of others, making it a unique characteristic that can be utilized to distinguish

TABLE 2

Data analysis of five different materials structured acetone detection sensor

| Materials | Structure type | Response time (s) | Operating temperature (° C.) | Sensitivity (%) | Detection Limit (ppm) |
| --- | --- | --- | --- | --- | --- |
| PPy—WO$_3$ (20%) | hybrid nanocomposites | NA | 90 | 3.34 × 10$^{-3}$ | 0.37 ppm [36] |
| Pt—InN | ultra-thin FET | NA | 200 | 5.07 | 0.4 ppm [37] |
| K$_2$W$_7$O$_{22}$ | nanostructure | 12.5 | 25 | 50.75% | 0.1 ppm [20] |
| Pd/TiO$_2$/p-Si | nanocrystalline | ~15 | 100 | 16 | 10 ppm [38] |
| Ni/InGaN/GaN | heterostructure | ~7.6 | 100 | 1.021 | 100 ppm [39] |

*1 µg/g = 1 ppm
*NA = Not Available

FIG. 5, further includes the sensing response to acetone based on the KWO sensor and the Pt—InN sensor. FIG. 5 (Pt—InN, bottom; KWO, top) shows that the KWO sensor demonstrates much higher sensitivity than the Pt—InN sensor does, with variable acetone concentrations from 0 to 20 ppm. In addition, the KWO sensor operates at room temperature without needing an external source of heat, while Pt—InN sensor needs to work under 200° C. All these indicate that the nanostructured KWO sensor is an optimal sensor device with less power consumption and higher sensitivity. Also, this sensor device is simple and easy to be fabricated at a cost reduction [40]. FIG. 6 exhibits that KWO also has good selectively on acetone. The main reason why nanostructured K$_2$W$_7$O$_{22}$ shows much better sensing performance on the detection of acetone is due to its specific material property—the room-temperature ferroelectric property (detailed discussion can be found in a published paper [41]), which can make the surface interaction between KWO and acetone much more efficient. Considering the sensing mechanism of the other four acetone sensors, they need to operate at higher temperatures (>100° C.) which are due to a surface oxidation reaction under the presence of acetone. [42].

acetone from other compounds for sensing purposes. Although there are already many papers as well as patents reporting the capability for acetone detection with satisfactory sensitivity (i.e., very low detection limit), the only products available on the market are from Ketonix [44] and GM Nameplate [45]. These products have been advertised to work for the detection of acetone in exhaled breath, however they are designed to just roughly reflect the acetone concentration in four levels indicated by four LED lights, with the lowest detection limit corresponding to about 7.7 ppm. The main purpose of these products is to monitor the fat loss after exercise. Although it has also been mentioned that these products can be used for monitoring diabetics, in view of the 1.7 ppm threshold for detecting diabetes and the 7.7 ppm detection limit of these products, they are not suitable for monitoring diabetics. More importantly, with such a detection limit, these products can't be used for the purpose of diagnosis. In other words, there is no one product available on the market at the present time that can effectively diagnose or monitor diabetes. The reason that there have been many papers and patents published but no products have been put onto the market successfully seems to be due to the limit of the sensing mechanism in most of the existing acetone sensors, which involves the use of a high temperature. The sensing mechanism of sensors operating at a high temperature is primarily based on a redox reaction, which needs to take place at a high temperature. This generates a critical technical drawback and brings about some other disadvantages such as high cost and issue of circuit integration, making these sensors practically unfeasible. The limitations mentioned above motivated us to seek new materials and mechanisms that can respond to acetone much more sensitively under realistic breath conditions so as to truly achieve the diagnosis and monitoring of diabetes through the analysis of exhaled breath. The material should have stable and excellent ferroelectric property at room temperature to attract high polar acetone molecules and cause the resistance change at room temperature (RT).

It is further appreciated in the art that diabetic ketoacidosis occurs in a significant proportion of patients with type II diabetes. [46]

Ketone bodies are a by-product of the fat metabolism process. Specifically when fat is metabolized the fatty acids are first transformed into acetyl-CoA and then depending on the level of glucose, acetyl-CoA is converted into acetoacetate which is further converted into beta-hydroxybutyrate and acetone. Since acetone is small and readily diffusible, acetone diffuses into the lungs and is exhaled in breath. Since production of acetone is related to fat metabolism, acetone excreted in breath is also proportional to fat loss. A subject in a state of ketosis is associated with an increase in breath acetone and include fat loss, ketogenic dieting, fasting, alcoholism and alcoholic binge drinking. [47-48]. It is possible that dietary and life style factors such as garlic consumption, caffeine green tea extract, disulfram administration, dry sauna, obesity and even cold can increase basal breath acetone by 1-4 ppm. Extreme fasting has been shown to increase breath acetone to around 170 ppm. [47].

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

(FIG. 1A), 200° C. (FIG. 1B), and 215° C. (FIG. 1C), respectively, and XRD patterns (FIG. 1D).

(FIGS. 7A and 7B) and for Sample 2 synthesized at 225° C. (FIGS. 7C and 7D). (Sample 2 has better acetone sensor performance than Sample 1.)

Figures 1A, 1B, 1C:
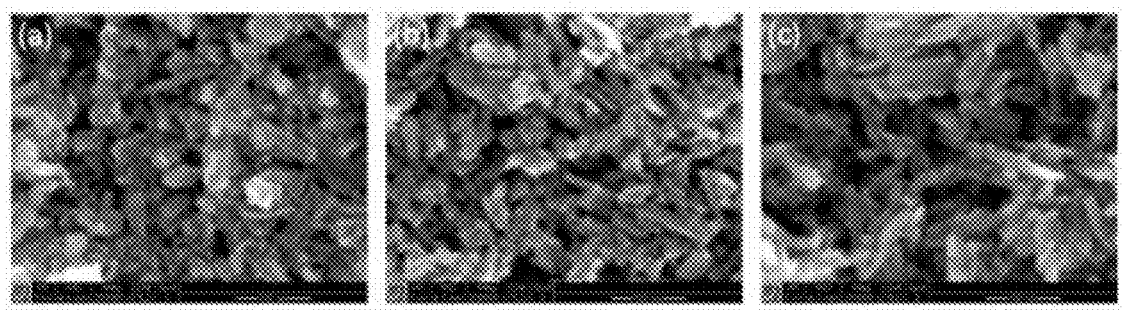
FIGS. 1A-1D show SEM images of $K_2W_7O_{22}$ nanorods synthesized at 185° C.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

Definitions

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a device" includes a plurality of such devices, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the term "subject" refers to a target in need of a diagnosis. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, whether male or female, are intended to be covered. A "patient" refers to a subject afflicted with a disease or disorder. The term "patient" includes human and veterinary subjects.

As used herein, the term "diagnosed" means having been subjected to a physical examination by a person of skill, for example, a physician, and found to have a condition that can be diagnosed or treated by the compounds, compositions, or methods disclosed herein. Such a diagnosis can be in reference to a disorder, such as diabetes, and the like, as discussed herein.

As used herein the term "ambient temperature" comprises typical temperatures living subjects are exposed to. Ambient temperatures range from approximately 0° C. to 550° C.

As used herein, the term "diabetes" can refer to Type I or Type II diabetes unless otherwise specified.

As used herein the term "state of ketosis" refers to a metabolic state of a subject where the body has insufficient access to glucose and is producing ketone bodies for energy from lipid stores. A subject may be in a state of ketosis for several reasons, some of these reasons, which are appreciated in the art, include consuming a ketogenic diet, lung cancer, alcoholism, alcoholic binge drinking, diabetes, fasting, and weight loss.

Embodiments

One embodiment of the present invention is a volatile organic compound (VOC) sensing device comprising: a volatile organic compound sensor component; a pressure sensor; and a microprocessor.

In a further embodiment of the present invention, the VOC sensor component is comprised of: a pair of electrodes; a moisture sensor; and nanostructured $K_2W_7O_{22}$.

In another embodiment of the present invention, the microprocessor collects moisture data, reads an acetone signal, calculates VOC concentration, generates electromagnetic signals, and displays the concentration of acetone in the sample in ppm.

In some embodiments of the present invention the VOC is acetone.

In a further embodiment of the present invention, the device includes an electric fan to refresh the air within the device.

In another embodiment of the present invention, a desiccant is placed in or connected to the device.

In one embodiment, the present invention relates to a method for diagnosing a subject as in a state of ketosis.

In another embodiment, the present invention further relates to diagnosing a subject as in a state of ketosis comprising having a subject breathe into a device comprising: an acetone sensor, a pressure sensor, and a microprocessor.

In various embodiments of the present invention, the state of ketosis is selected from a ketogenic diet, lung cancer, alcoholism, alcoholic binge drinking, diabetes, fasting, weight loss, or combinations thereof.

In some embodiments of the present invention, the state of ketosis is type I or type II diabetes.

A further embodiment of the present invention is a method for diagnosing a subject as having diabetes comprising having a subject breathe into a device comprising: an acetone sensor, a pressure sensor, and a microprocessor, and diagnosing the subject with diabetes when the acetone concentration is greater than or equal to about 1.7 ppm.

Another embodiment of the present invention includes a method of making $K_2W_7O_{22}$ nanocrystals comprising: making a solution comprising: $Na_2WO_4$, Oxalic acid, $K_2SO_4$, HCl, autoclaving the solution; and growing crystals at 160, 180, 210, or 225° C. for about 24 hours.

EXAMPLES

Materials & Methods

Example 1: Material Synthesis

Figure 1D:
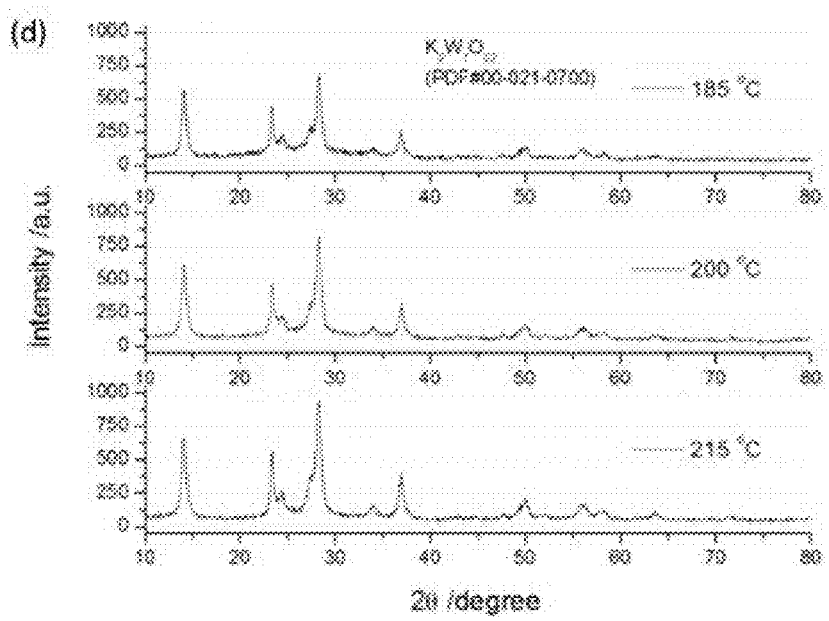
Figure 2A:
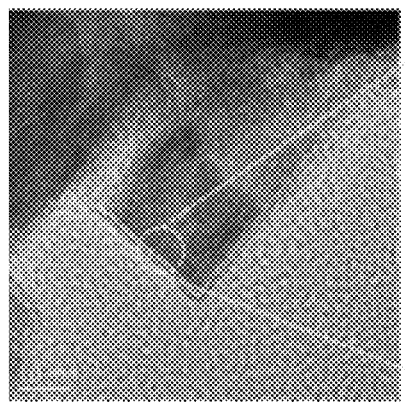
FIGS. 2A and 2B show HR-TEM images of $K_2W_7O_{22}$ nanorods.
Figure 2B:
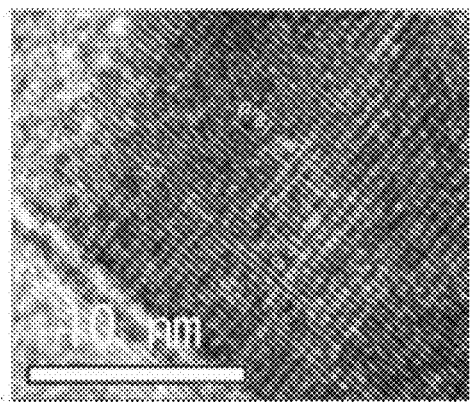

The nanostructured $K_2W_7O_{22}$ was synthesized with a hydrothermal method [17-19]. It uses a precursor solution containing $Na_2WO_4$, oxalic acid, $K_2SO_4$, and HCl. The composition of this material has been analyzed with XPS, revealing that the atom ratio of K:W:O is 2:7:22. Further study demonstrated that the geometric structure of the nanorods could be tuned by varying the temperature for hydrothermal growth; higher temperature led to longer nanorods with better crystallinity (FIG. 1). HR-TEM characterization indicated that the nanorods were single crystals with the axial lattice-fringe distance being 0.31 nm and the radial lattice-fringe distance being 0.61 nm (FIG. 2). However, due to the lack of information regarding the crystal structure of $K_2W_7O_{22}$ in the literature, the lattice planes corresponding to these lattice-fringe distances cannot be determined at this stage.

Example 2: Characterization of Acetone Sensing Performance

Figure 3:
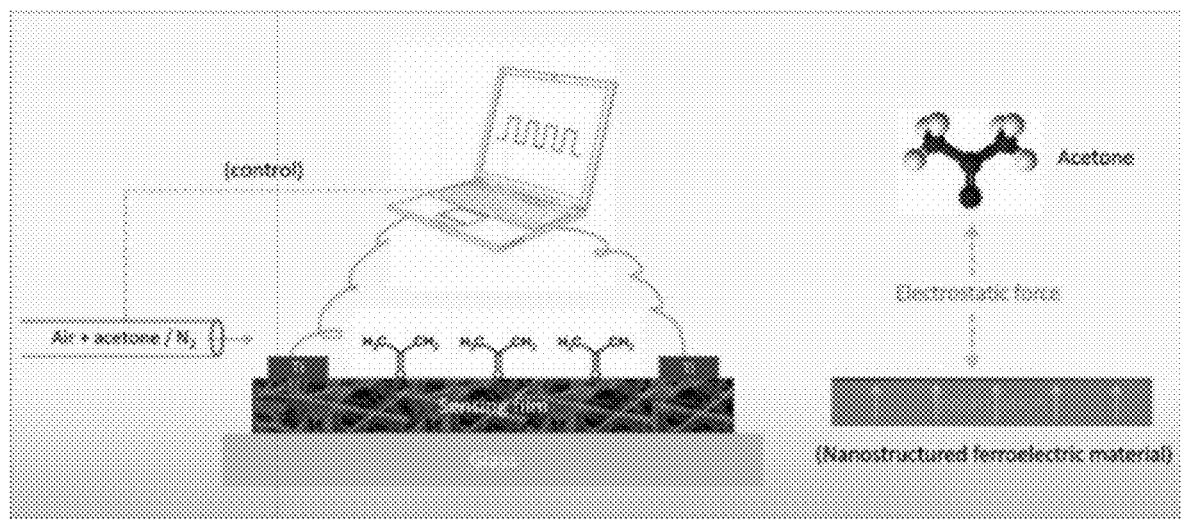
FIG. 3 shows a chemiresistive sensor testing system (left) and a schematic drawing showing electrostatic attraction between acetone molecules and a ferroelectric material (right).

The acetone sensing performance of the materials optimized based on the investigation of the ferroelectric property and the simulation of acetone molecule adsorption on different exposed facets have been characterized with a programmable chemiresistive gas sensor measurement system (FIG. 3), which has been fully developed and has the capability of precisely controlling the acetone concentration, gas flow rate, and the humidity. [20, 21] In detail, the variation of acetone concentration from 0 ppm to 50 ppm is obtained by diluting 50 ppm pure acetone with dry air at the required ratio. The resistance change and response time of the sample are determined by measuring its resistance between the metal contacts with an electrometer (Keithley 6514) when the gas applied to the sensor film cycled between air with vapor and dry air.

Example 3: A New Material, Nanostructured $K_2W_7O_{22}$ has been Developed

Figure 4A:
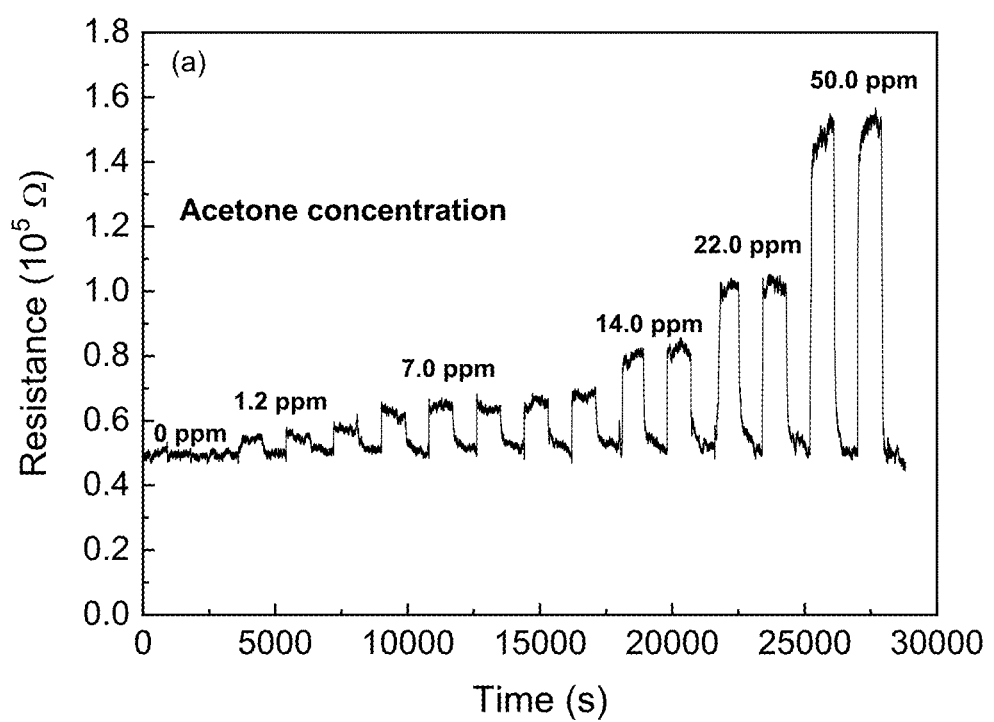
FIGS. 4A-4B show performance of acetone sensor constructed with $K_2W_7O_{22}$ nanorods, with FIG. 4A showing dependence of the sensing film's resistance change on the concentration of acetone, and FIG. 4B showing the response time of the sensor corresponding to 50 ppm acetone.
Figure 6:
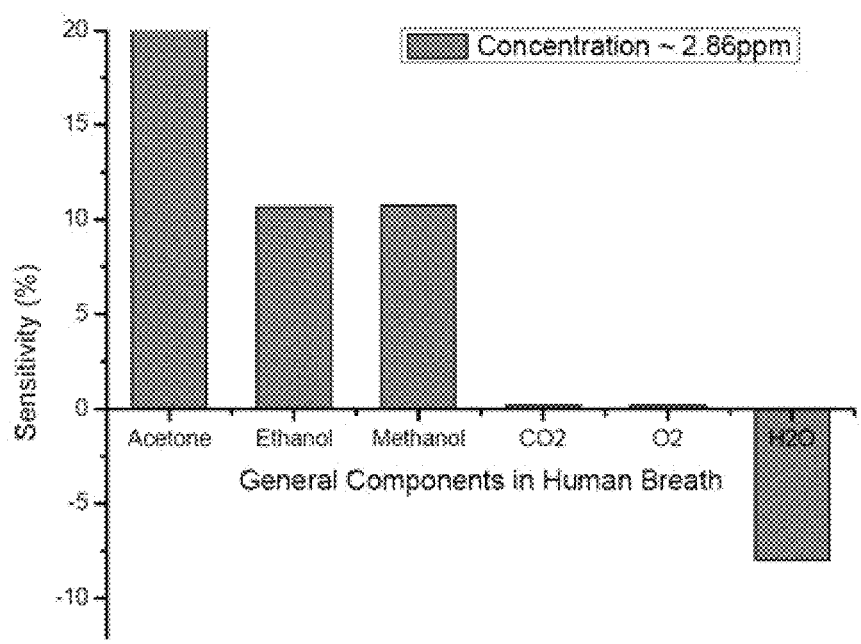
FIG. 6 shows sensing response of $K_2W_7O_{22}$ nanorods to vapors of acetone, methanol, ethanol, water, $CO_2$ and $O_2$ at concentration of 2.86 ppm.
Figure 7A:
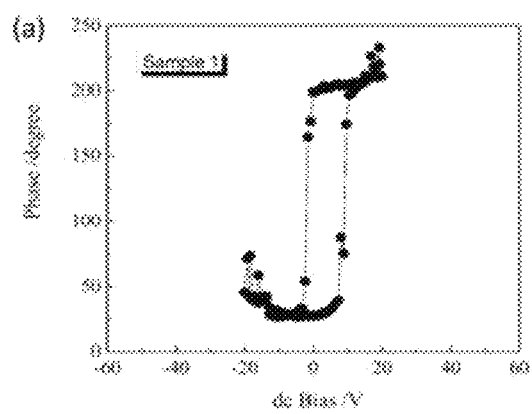
FIGS. 7A-7D shows PFM phase and amplitude hysteresis loops, for Sample 1 synthesized at 180° C.
Figure 7B:
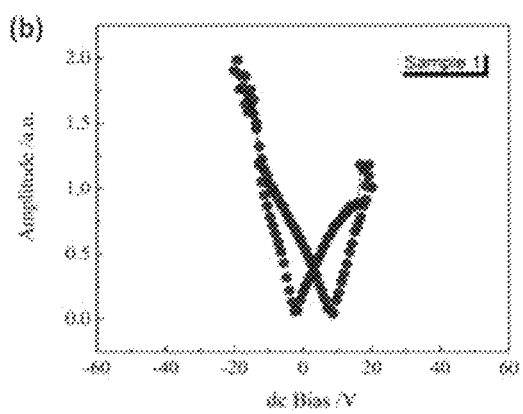
Figure 7C:
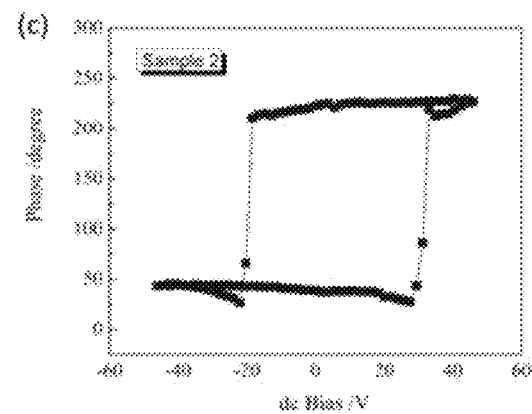
Figure 7D:
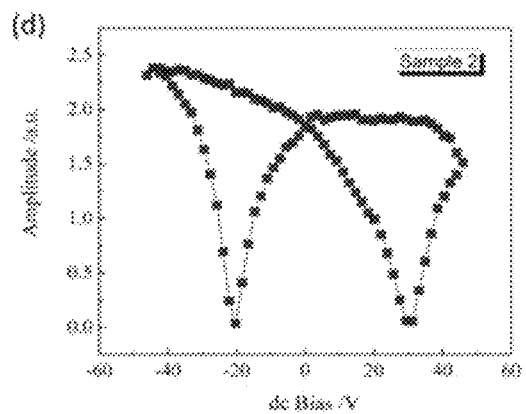
Figure 14:
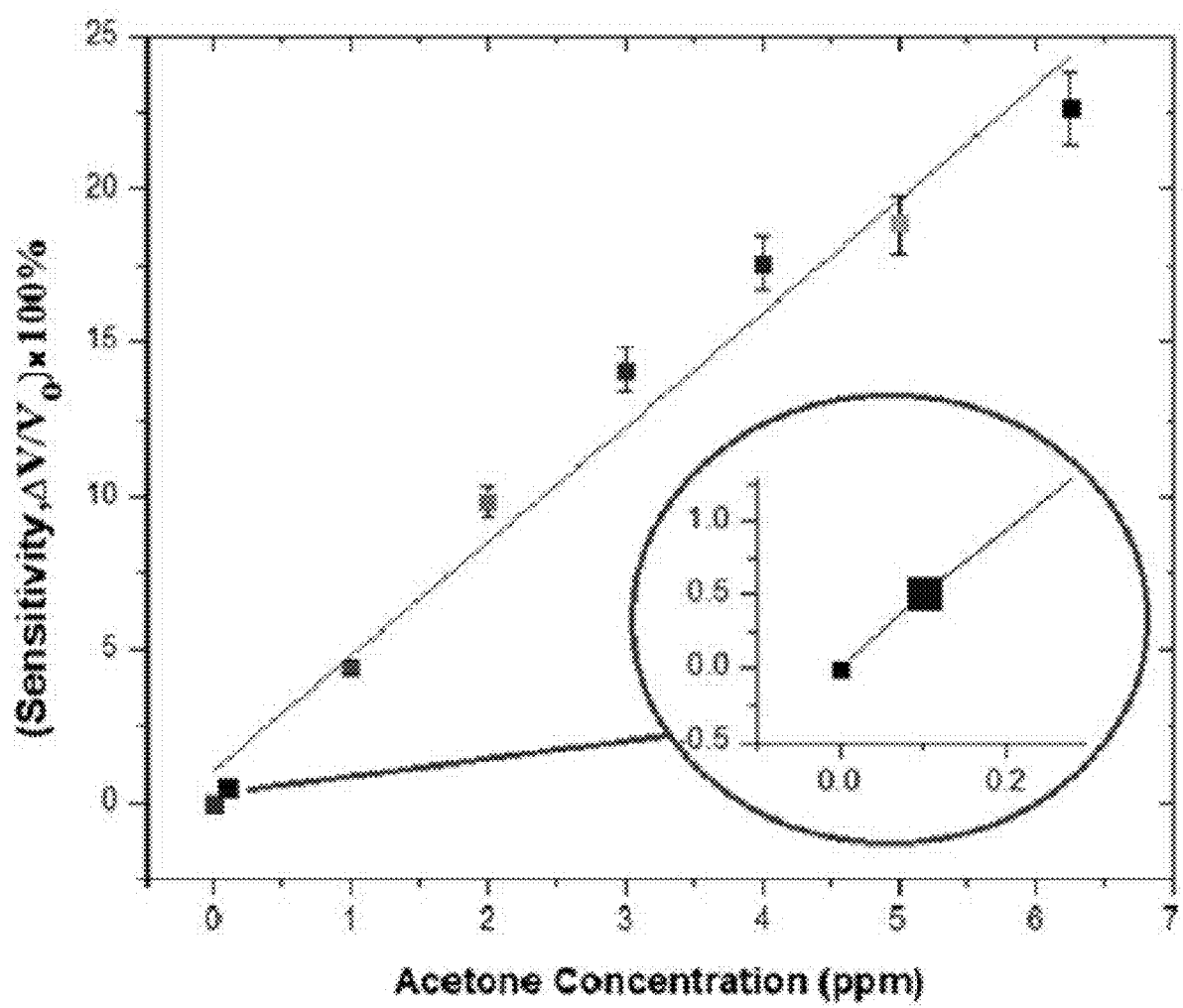
FIG. 14 shows sensitivity readings due to change in concentration of acetone for 0-6.25 ppm.

The performance of the nanostructured $K_2W_7O_{22}$ for sensing acetone has been studied by varying the acetone concentration from 0 ppm (i.e., no acetone) to 50 ppm, where the acetone was carried by air at a relative humidity (RH) of ~30%. It was shown that (1) the resistance of sensing film changes upon acetone adsorption, (2) the resistance change is greater when the acetone concentration is higher, and (3) there is no difficulty in sensing acetone with a concentration as low as 2.0 ppm (FIG. 4A). A fitting of the evolution of resistance versus time shows that, for 50 ppm acetone, the sensor's response time is only ~12 s (i.e., the time over which the resistance change reaches 90% of the saturated value) (FIG. 4B), meaning that the sensor shows promise for high-speed applications. Considering 2.0 ppm detection limit is not low enough to sensitively detect acetone when its concentration is lower than 1.7 ppm, it was found that $K_2W_7O_{22}$ crystalline structure and material properties can be a factor to improve the sensor detection limit. Also, the control and signal collection circuit can be modified to realize weak signal detection with high signal to noise ratio. As shown in FIG. 14, the detection limit of $K_2W_7O_{22}$ can be down to 0.1 ppm of acetone. This is much lower than the threshold of diabetes, 1.7 ppm. Considering realistic breath conditions, the sensor specificity was also determined (FIG. 6) to the compounds commonly existing in human breath, such as ethanol, methanol, $CO_2$, $O_2$, and water. The results show that $K_2W_7O_{22}$ nanorods exhibit best sensitivity to acetone at the same operating condition. This makes the nanostructured $K_2W_7O_{22}$ a very competitive material for use in breath analyzer for detecting exhaled acetone.

Example 4: The Semiconducting Property of the $K_2W_7O_{22}$ was Studied Using the Hall Effect Technique It showed that $K_2W_7O_{22}$ is a p-type semiconductor and the carrier concentration and mobility are $3.26 \times 10^{17}$ cm$^{-3}$ and $7.5 \times 10^{-2}$ cm$^2$V$^{-1}$ s$^{-1}$, respectively. A semiconductor that is p-type means that its majority carriers are holes. This can explain why the resistance increases upon the adsorption of acetone molecules in FIG. 4A, i.e., acetone as a reducing gas can transfer electrons to $K_2W_7O_{22}$; the electrons recombine with the holes in $K_2W_7O_{22}$, causing a decrease in the concentration of holes and thus resulting in a resistance increase. This is in agreement with what has been reported in literature: for a p-type semiconductor, a reducing gas usually causes a resistance increase. [37] Using a piezoresponse force microscope (PFM), a study of the ferroelectricity of nanostructured $K_2W_7O_{22}$ synthesized at different temperatures was also determined: Sample 1 at 185° C., and Sample 2 at 225° C. The results shown in FIG. 7 display well-defined phase hysteresis curves and amplitude butterfly loops, indicating that $K_2W_7O_{22}$ possesses ferroelectric character at room temperature. Comparing the phase hysteresis for the two samples, it can be seen that, for Sample 1, the PFM phase changes by 180° at the coercive voltages of −2.8 V and 10 V, whereas for Sample 2 the phase change occurs at very different voltages, −20.6 V and 32.8 V. These results suggest that the ferroelectric property of $K_2W_7O_{22}$ nanorods is dependent on the processing parameters for material synthesis, which affect both the crystal structure and the geometric structure of the material: higher temperature results in better crystallinity and longer nanorods. In other words, the ferroelectric property of the $K_2W_7O_{22}$ nanorods is tunable, with consideration to the material's composition, crystal structure, and geometric structure. In the experiment, Sample 2 was synthesized at a temperature higher than Sample 1, and has been observed to have higher sensitivity to acetone. This further evidence that the room-temperature ferroelectric property of $K_2W_7O_{22}$ nanorods results in excellent sensing response to acetone.

Example 5: KWO Synthesis and Imaging

Figure 8:
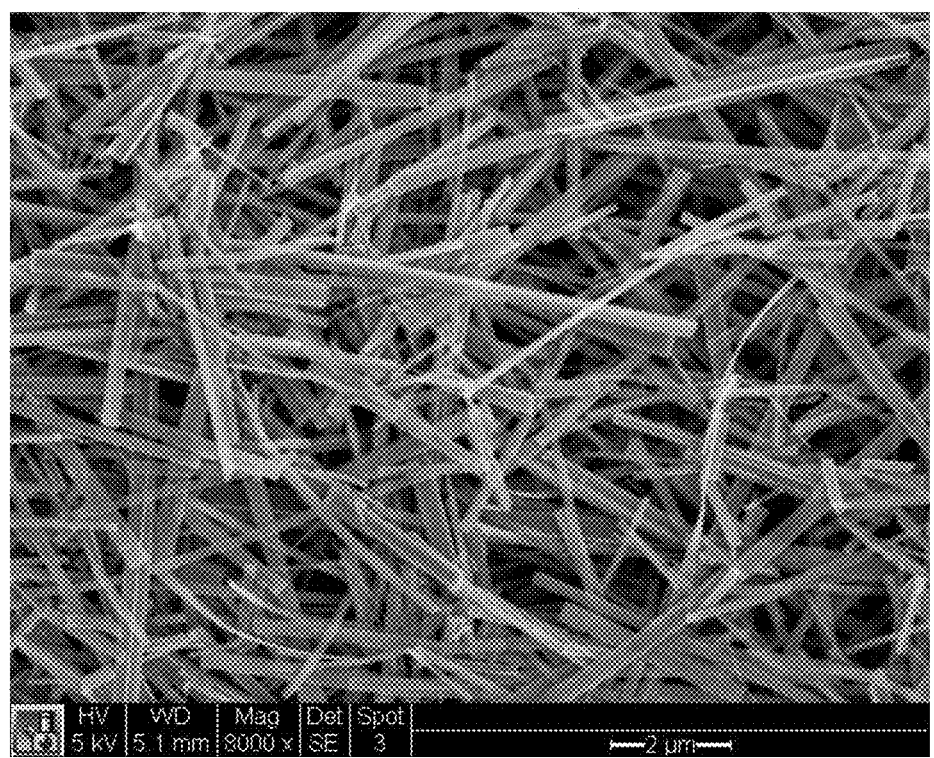
FIG. 8 shows the morphology and crystal structure of sensor material $K_2W_7O_{22}$ nanorods synthesized at 225° C.

The single crystalline nanostructured KWO was synthesized by a hydrothermal technique [17,61]. Briefly, a precursor solution containing $Na_2WO_4$, oxalic acid, $K_2SO_4$, and HCL is made. This solution is then put into a 30 mL autoclave for synthesis. KWO samples were grown at 225° C. for 24 hours. The as-synthesized nanostructured KWO were dispersed in ethanol to form a suspension and dropcasted on glass substrates to form a thin film with about 10 μm in thickness. The morphology of the KWO film was studied with scanning electron microscopy (SEM) (FIG. 8) and the film shows a highly porous structure made of a three-dimensional mesh of randomly orientated and interconnected nanorods. The average length of the nanorods is about several micron and the diameter of nanorod is about 10 nm, which are adjustable through synthesis conditions. Electric contact pads made of gold are sputtering deposition onto the thin film. The sensing response of KWO by exposing acetone is determined by measuring its resistance between the metal contacts with an electrometer (Keithley 6514). More information regarding KWO to detect acetone can be found in published literatures [20,41,21].

Figure 9:
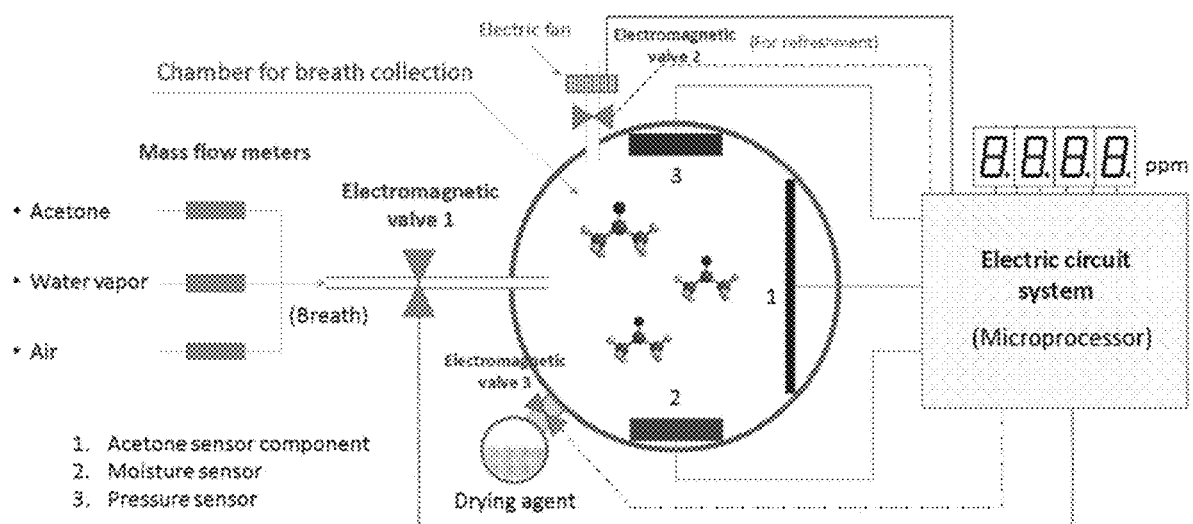
FIG. 9 shows a schematic drawing showing the structure of a breath analyzer consisting of a stainless steel chamber for the collection of breath and an electric circuit system for the analysis of the breath.

FIG. 9 is a schematic depicting one possible set-up for a device of the present invention.

Example 6: Circuit Design

Figure 10:
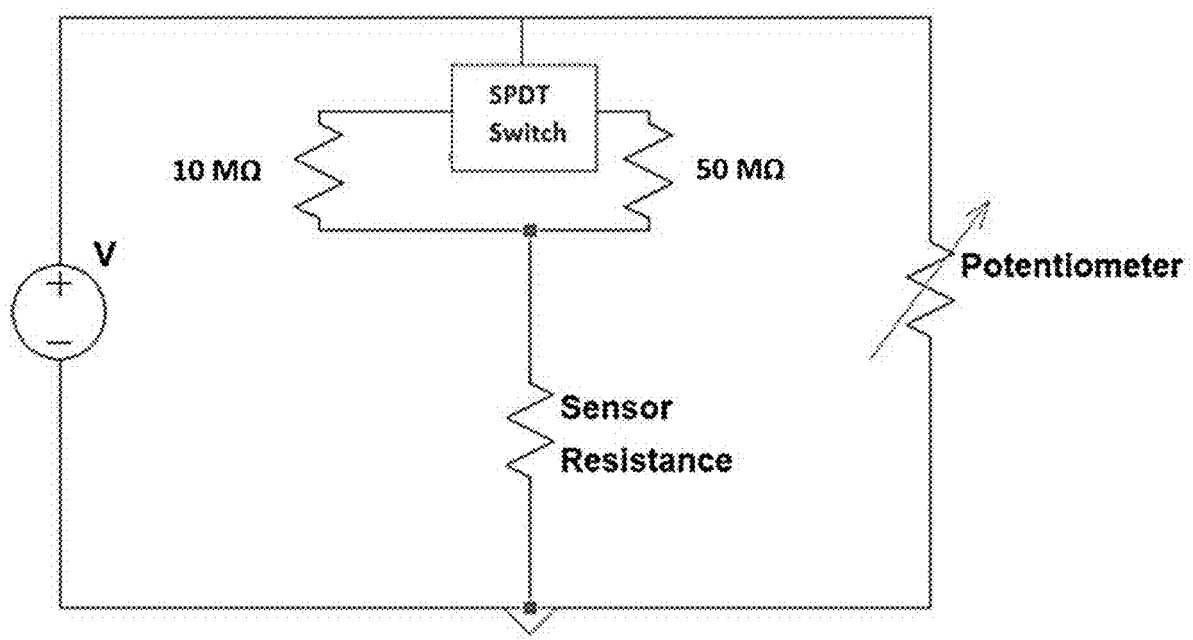
FIG. 10 shows a schematic diagram of a Wheatstone bridge for sensor circuits.
Figure 11A:
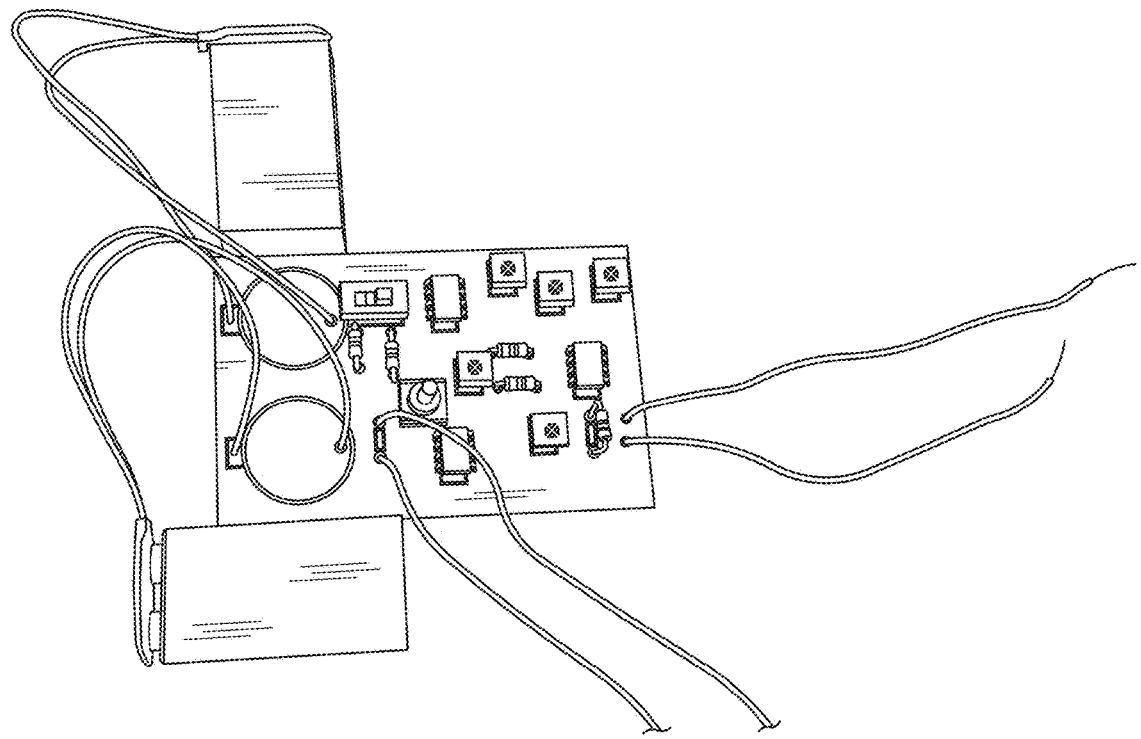
FIG. 11A shows a PCB layout of a gas detection circuit.
Figure 11B:
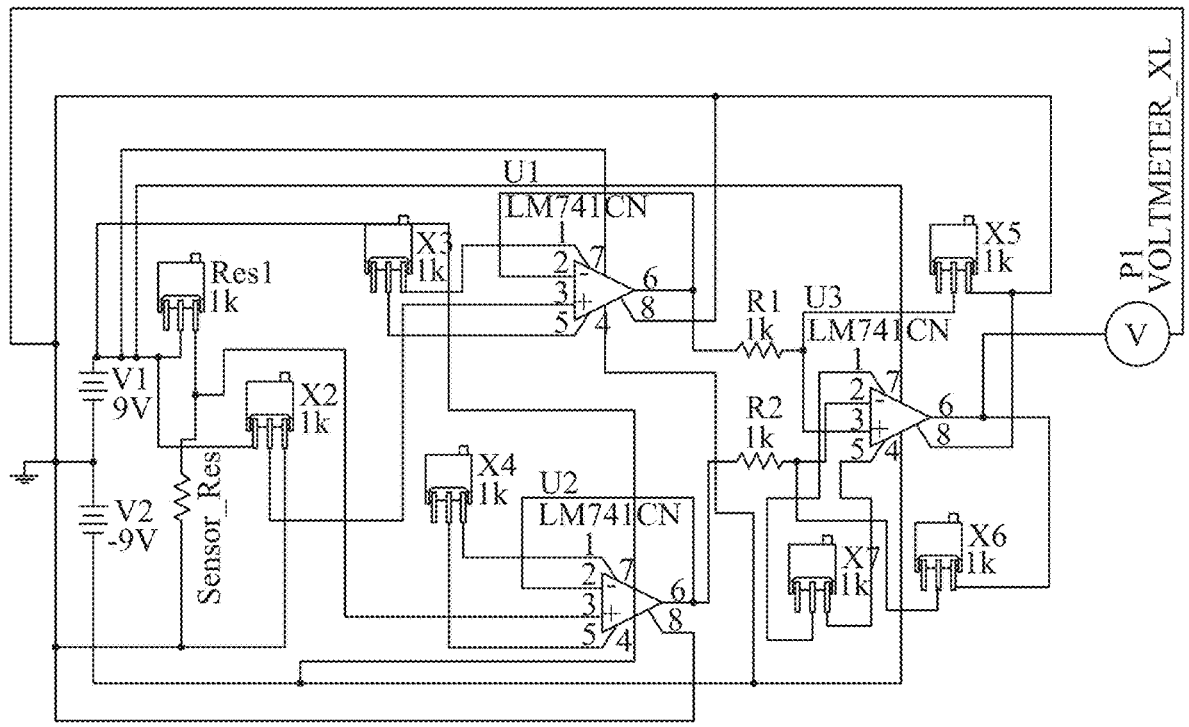
FIG. 11B shoes a schematic diagram of the amplified circuit of FIG. 11A.

To detect the signal, a cost-efficient circuit was made with available components such as resistors, potentiometers, LM741 CNNS op-amp [43], and 9V battery. The printed circuit board (PCB) was designed from OSHPARK [44]. As shown in FIG. 10, 10 MΩ and 50 MΩ resistors were connected with SPDT switch [45] for compatible adjustment with the sensor resistance while testing different ranges of acetone concentration. The other branch of the Wheatstone bridge was introduced with a potentiometer to make zero correction of the circuit. Buffer amplifiers [46] were introduced in the circuit to avoid impedance problem and to get unity gain. Because the signal from sensor detection is weak, a differential amplifier was used to amplify the signal. The voltages were taken from the two branches of the Wheatstone bridge. The amplification ratio was set up in accordance with the range of acetone detection. For instance, to detect low concentration of acetone (0-5) ppm, the signal was amplified 10 times. FIG. 11 (a) shows an embodiment of a PCB circuit board. Two 9V batteries were used to make +9V and −9V. The amplification of the signal was set in between the range of −9V to +9V and the output was clipped beyond that range. The output from the circuit was measured on an electrometer. FIG. 11 (b) shows the schematic diagram of the circuit.

Example 7: Experimental Design

Figure 12:
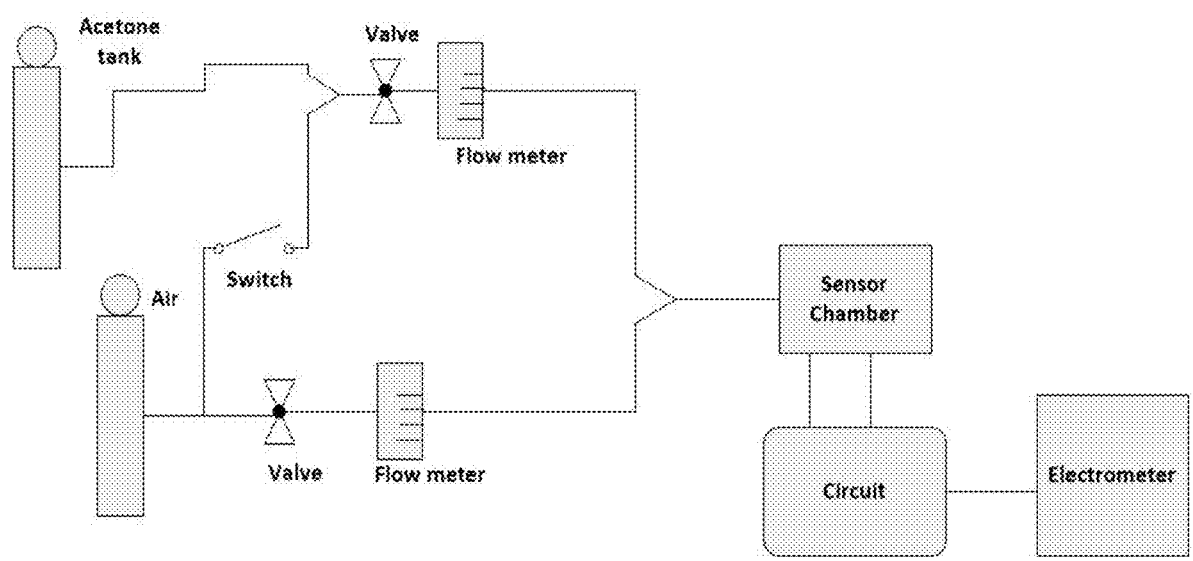
FIG. 12 shows a block diagram of a testing system.

The sensor was tested with 0-6.25 ppm and 0-50 ppm concentration of acetone. The primary goal was to check the sensitivity of the circuit while the concentration of acetone is low (0-6.25 ppm). The other goal was to make sure that the circuit can functionally work nicely in a broad range of acetone concentration, 0-50 ppm. FIG. 12 shows the sketch of the whole testing system. Acetone gas, supplied from the tank is pure acetone mixed with nitrogen at the concentration of 50 ppm. The concentration of acetone can be diluted via mixing 50 ppm acetone with air. The sensor was put in a metal box and connected to the circuit for signal detection and collection. The circuit output was monitored from the electrometer and collected via computers.

Example 8: Sensing Mechanism

Figure 13:
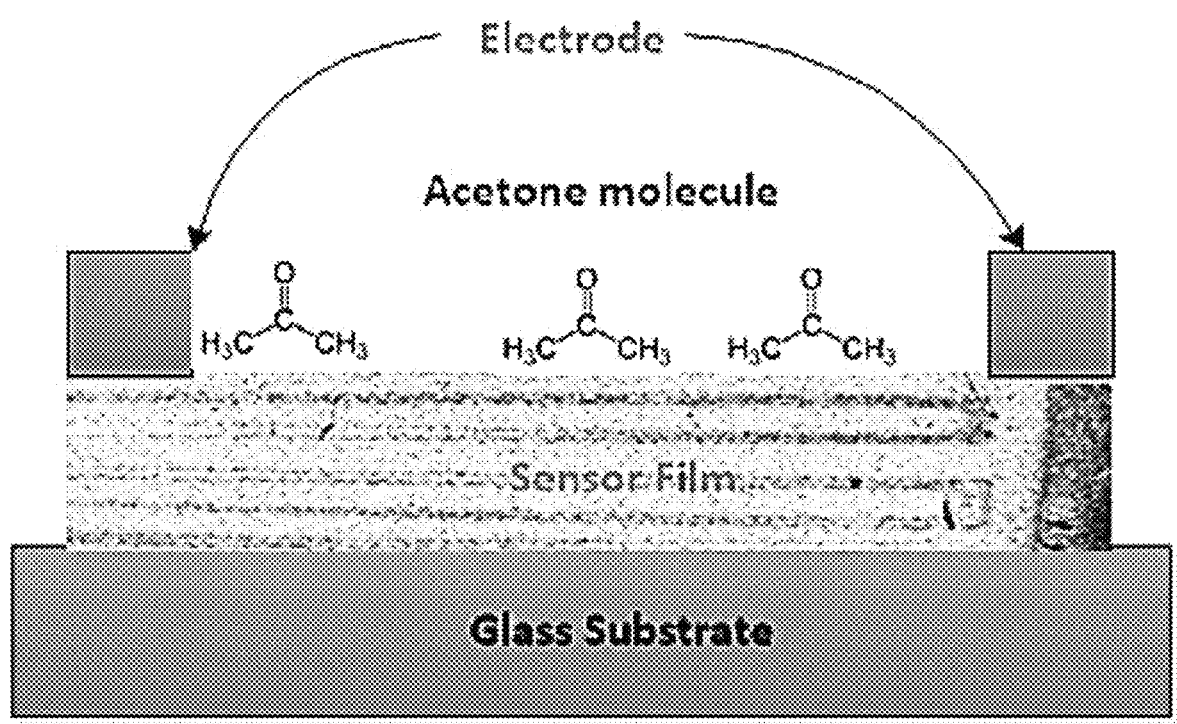
FIG. 13 shows the electrostatic attraction between acetone molecules and the KWO sensor.

The KWO sensor is sensitive to acetone gas. FIG. 13 shows the sensing interaction between the acetone molecule and the KWO sensor. Nanostructured KWO was measured to be a p-type semiconductor via a Hall effect measurement (Ecopia HMS-3000). Also, it showed good room-temperature ferroelectric properties [26]. All these unique properties of KWO can make it effectively attract high polar acetone molecules and result in an increase of the resistance [41, 49, 50]. Therefore, a KWO sensor can also be called chemiresistive sensor.

Example 9: Sensitivity

Sensitivity is the most important parameters for evaluating the sensing performance of sensors [51]. Sensitivity is defined as the variation in current ratio for specific gas concentration. If $I_{gas}$ and $I_{air}$ are the current values of the sensor, then the sensitivity, S [26] is:

$$\text{Sensitivity}(S) = \frac{I_{gas} - I_{air}}{I_{air}}$$

Sensitivity can be also measured in terms of voltage [52] and resistance [53]. Two sets of data was collected from the testing system. FIG. 14 shows the sensitivity in terms of voltage that was found for the acetone concentration from 0 to 6.25 ppm. The sensitivity shows a linear relationship between the detected signal to the acetone from 0 to 6.25 ppm. Also, FIG. 14 reveals an improvement of the sensitivity of KWO sensor when detecting acetone. The sensitivity was about 50.75% even when the concentration of acetone was only about 0.1 ppm.

TABLE 4

Sensitivity comparison between improved circuit measurement system (sample 1) and previous resistance measurement system (sample 2) for acetone concentrations of 0-6.25 ppm.

| Acetone Concentration (ppm) | Sample 1 (Sensitivity, ΔV/Vo) × 100% | Sample 2 (Sensitivity, ΔR/Ro) × 100% |
| --- | --- | --- |
| 0 | 0 | 0 |
| 1 | 4.411 | 0.1 |
| 2 | 9.823 | 0.2 |
| 3 | 14.117 | 0.225 |
| 4 | 17.588 | 0.245 |
| 5 | 18.882 | 0.28 |
| 6.25 | 22.647 | 0.29 |

Example 10: Sensing Performance

The sensing performance of the KWO sensor was compared to low concentrations of acetone, 0-6.25 ppm, with and without using improved circuits as the signal collection. Table 4 shows the detection limit and sensitivity while the KWO sensor system employed the optimized detecting circuit. For example, the sensitivity of 1.0 ppm of acetone with the improved circuit was 441.1%, while the sensitivity without the improved circuit at 1.0 ppm of acetone was only 10%. The results indicated that the improved circuit significantly improved the sensitivity and detection limit of the KWO sensor. This is a very important improvement, in particular, considering the KWO sensor in application for the purpose of early stage type-1 diabetes diagnosis.

Figure 15:
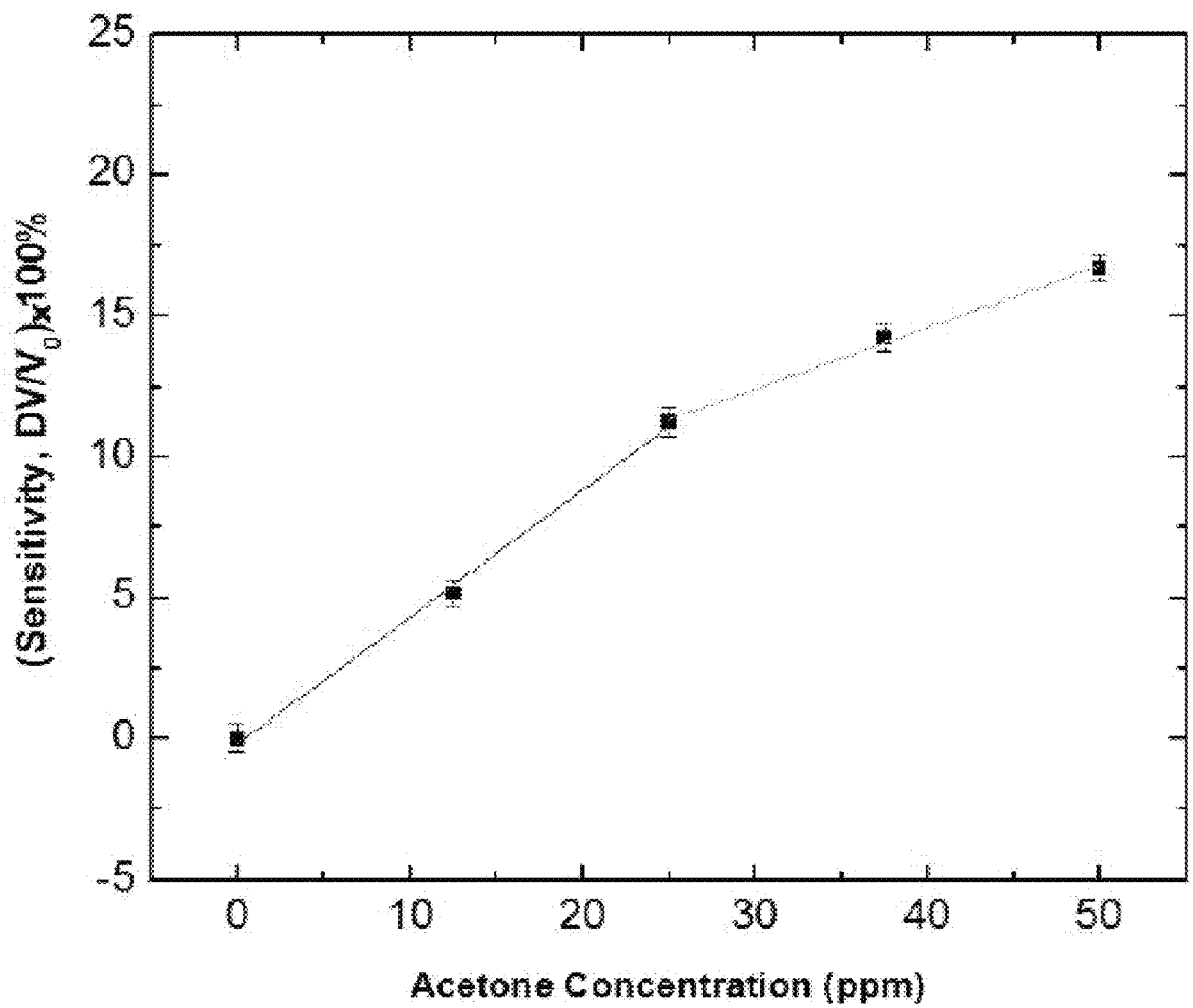
FIG. 15 shows sensitivity readings due to changes in concentration of acetone for 0-50 ppm.

Example 11: The Voltage Change for the Acetone Concentration from 0 to 50 ppm was Also Measured FIG. 15 shows the sensitivity for the acetone concentration from 0 to 50 ppm. The results indicated a quite linear relationship between the sensitivity and the concentration of acetone from 0 to 25 ppm for the KWO sensor to detect acetone. However, when the concentration of acetone was higher than 25 ppm, the increase of sensitivity was a little bit offset with the increase of acetone concentration. This was because the resistance of the KWO sensor was higher than 50 MW while it was exposed with a higher concentration of acetone such as more than 25 ppm. Such a high resistance made the output voltage from the voltage divider branch unable to make a proportional change for the corresponding acetone concentration. Therefore, it was difficult for the circuit to show a broader linear response with the change of acetone concentration from 0 to 50 ppm.

Example 12: Sensing Response Comparison with Pt—InN

Figure 4B:
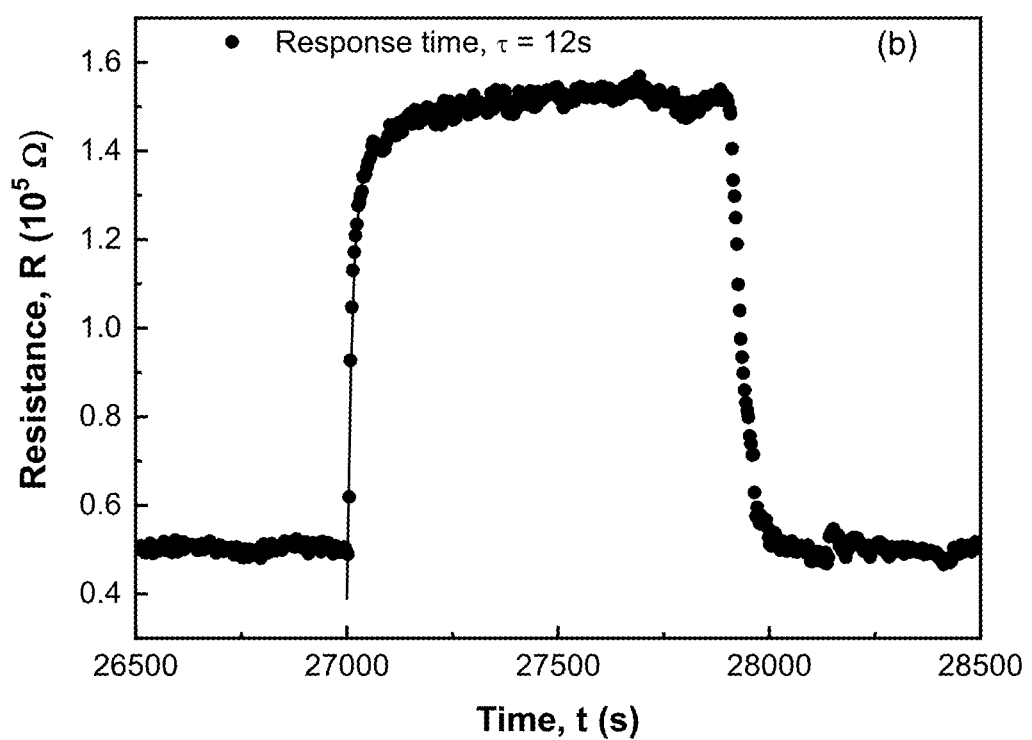
Figure 5:
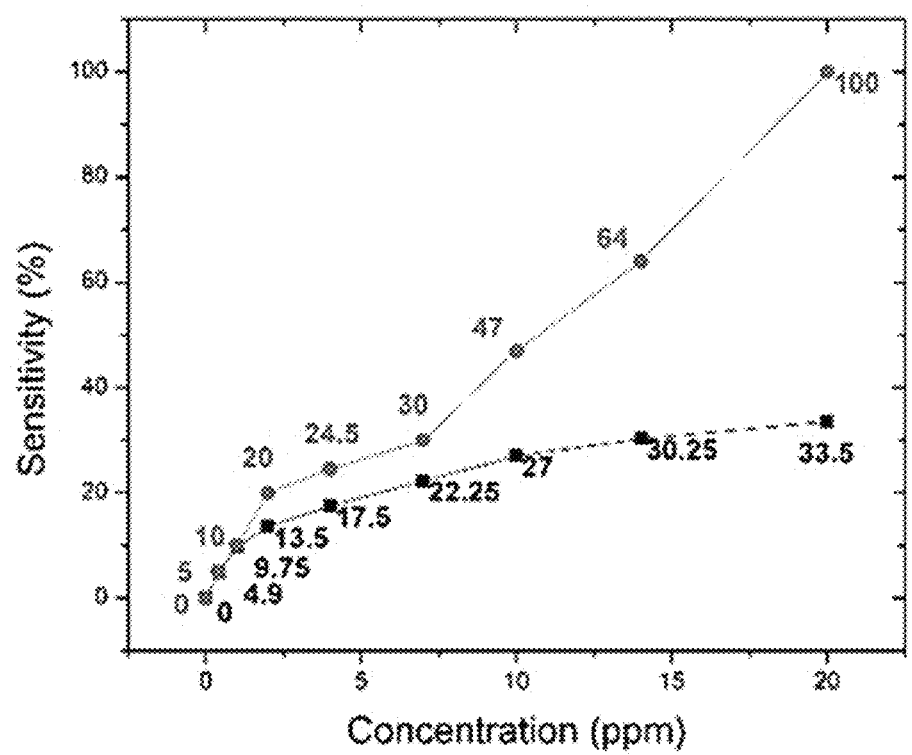
FIG. 5 shows sensing response of KWO and Pt—InN sensors to detect acetone with concentration from 0 to 50 ppm.

In FIG. 5, the sensing response to acetone focused on the materials of KWO and the Pt—InN (This graph is based on data in FIG. 4b in reference [26] in black and 3a in reference [20] in red). FIG. 5 shows that the KWO based chemiresistive sensor demonstrates much higher sensitivity than the Pt—InN based sensor has, while acetone concentrations vary from 0 to 20 ppm. In addition, the KWO sensor can operate at room temperature without requiring any external source of heat, while Pt—InN sensor needs to work under 200° C. All these indicate that the nanostructured KWO based acetone sensor is an optimal device with less power consumption and higher sensitivity. Also, the KWO sensor device is simple and easy to be made [40] due to its chemiresistive sensing mechanism. The main reason why nanostructured $K_2W_7O_{22}$ shows much better sensing performance on the detection of acetone can be explained by its high surface to volume ratio due to the nanoscale and porous structure and the specific material property—the room-temperature ferroelectric property of KWO (detailed discussion can be found in a published paper [41]). All of these properties result in an efficient surface interaction between KWO and acetone. While, the sensing processes based on the other four acetone sensors, all need to operate at an evaluated temperatures (>100° C.). This is mainly due to a surface oxidation reaction between the materials and acetone [42, 54]. In a word, according to above discussion, it reveals that the material and structure properties play the most important role in detecting acetone. Since as-fabricated nanostructured KWO has a room-temperature ferroelectric property and high surface area [20, 41], it provides an effective surface to sensitively interact with high dipole moment molecules such as acetone even at a low operating temperature.

Example 13: KWO Synthesis Methods

KWO is grown using the hydrothermal method. [19, 20] A precursor solution containing $Na_2WO_4.2H_2O$ (95%, Alfa Aesar), oxalic acid dihydrate (>99%, VWR), $K_2SO_4$ (>99%, VWR), and HCl (36-38%, Aqua Solutions Inc.) was made. This solution was then put into a 30 mL autoclave for synthesis. KWO samples were grown at 160, 180, 210, and 225° C. for 24 hours. Samples used for acetone sensing tests were applied to a sensor slide by blade coating and then annealed at 350° C.

Example 14: X-Ray Diffraction Spectrum (XRD)

X-ray diffraction was obtained using a Bruker AXS D8 Discover to study as-synthesized KWO crystalline structure. Samples were made by coating a paste made from KWO and ethanol on glass substrates. A diffraction pattern was gathered from a 2-Theta of 5° to 90° C.

Figure 16:
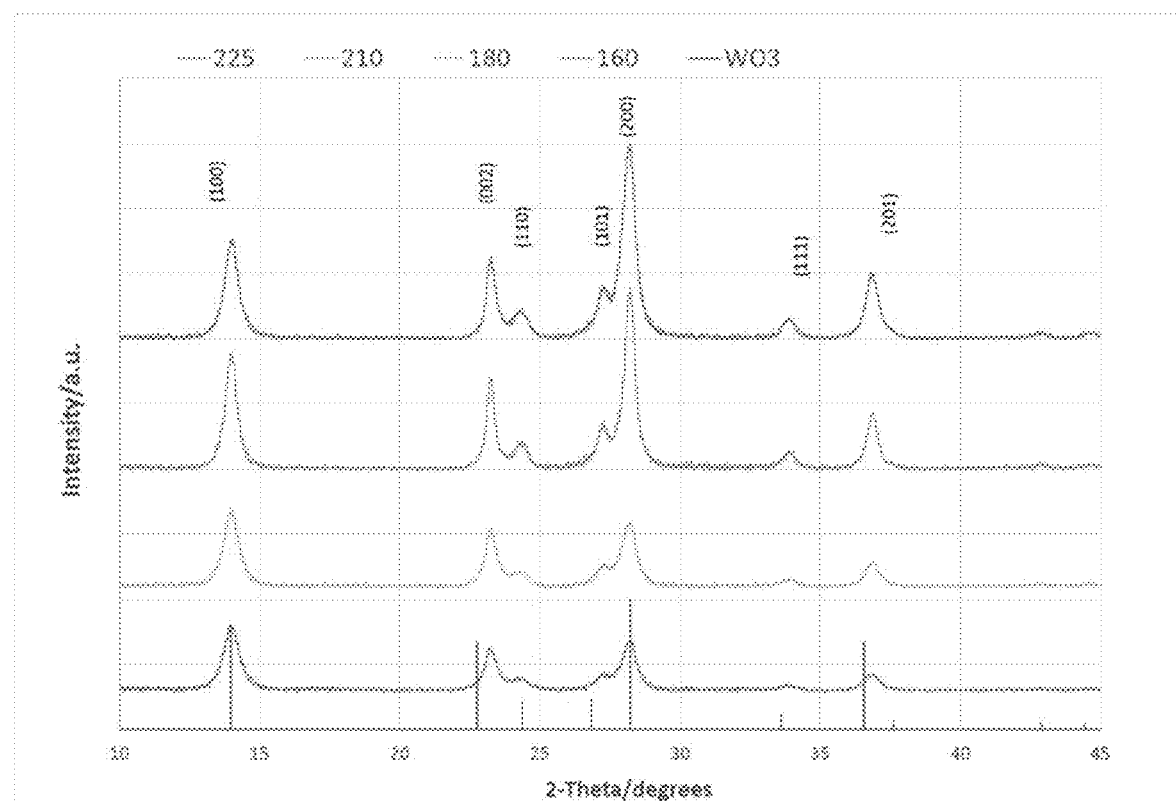
FIG. 16 shows XRD spectra of KWO growing at 160, 180, 210, and 225° C. and standard $WO_3$.
Figure 17:
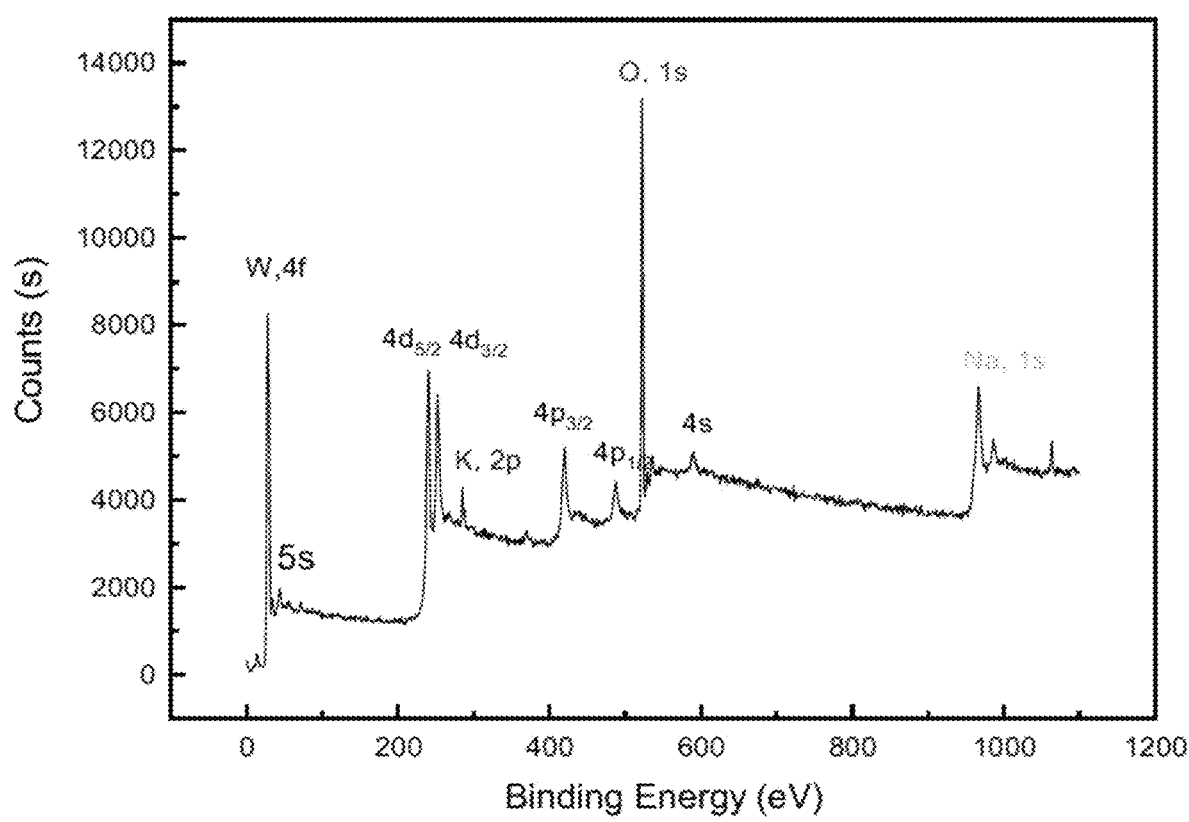
FIG. 17 shows XPS spectrum of $K_2W_7O_{22}$ nanorods.
Figure 18:
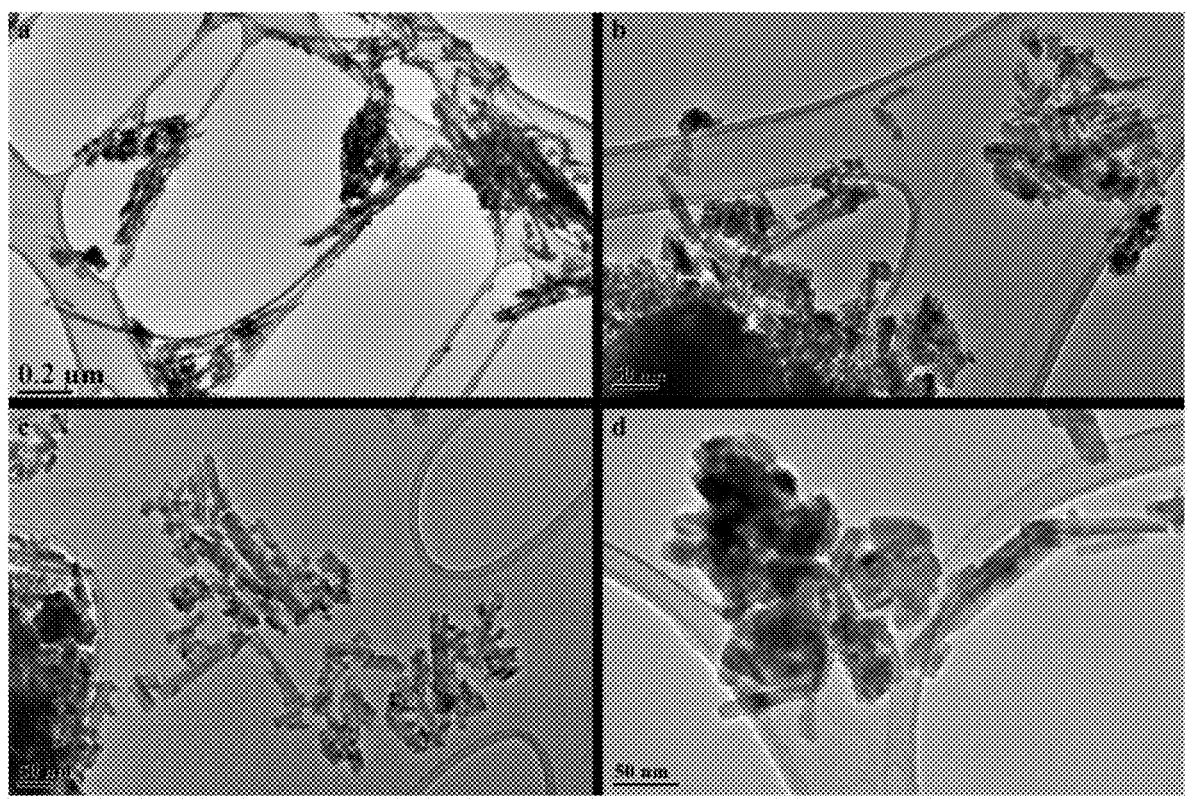
FIG. 18 shows HRTEM image of KWO samples grown at (a) 225, (b) 210, (c) 180, (d) 160° C.

FIG. 16 shows the XRD spectra of KWO grown at 160, 180, 210 and 225° C. The individual peak's 2-θ values found were: 14.013, 23.265, 24.339, 27.269, 28.175, 33.896, and 36.843 corresponding to the crystal indices of (100), (002), (110), (101), (200), (111), and (201), respectively. It was found that the crystal structure of KWO was similar to results found for other hexagonal tungsten oxides used for gas sensing. [57, 58, 19] The peak positions remain constant with respect to growth temperature indicating that the growth temperature did not alter the crystal structure. The main differences that can be observed in these samples from XRD are 1) stronger peaks are observed for samples grown at higher temperatures, and 2) the relative peak intensities of (200) and (201) facets become much more intense with respect to other peaks as the growth temperature was increased. In summary, nanorods grown at higher temperature presented higher crystallinity, and the increase in the (200) peak indicates that it is the growth direction. XPS was used to find the molar ratio of the as-synthesized nanorods to be sure that it matched the $K_2W_7O_{22}$ of previous research. [41] The values given in Table 5 show that the molar ratio of the material obtained is very close to the 2:7:22 expected. A detailed XPS spectrum, as shown in FIG. 18, further proves that the relative composition of the as-synthesized KWO.

TABLE 5

XPS Data of as-synthesized KWO.

| | PEAK (BE) | HEIGHT (CPS) | FWHM (EV) | AREA (P) (CPS.EV) | ATOMIC % |
|---|---|---|---|---|---|
| $W_{4F}$ | 36.36 | 421721.42 | 4.08 | 1798872.21 | 23.41 |
| $O_{1S}$ | 530.34 | 334091.36 | 2.59 | 995253.52 | 68.46 |
| $K_{2P}$ | 293.29 | 38855.81 | 2.70 | 168932.44 | 6.05 |

Example 15: Transmission Electron Microscopy (TEM)

Figure 19:
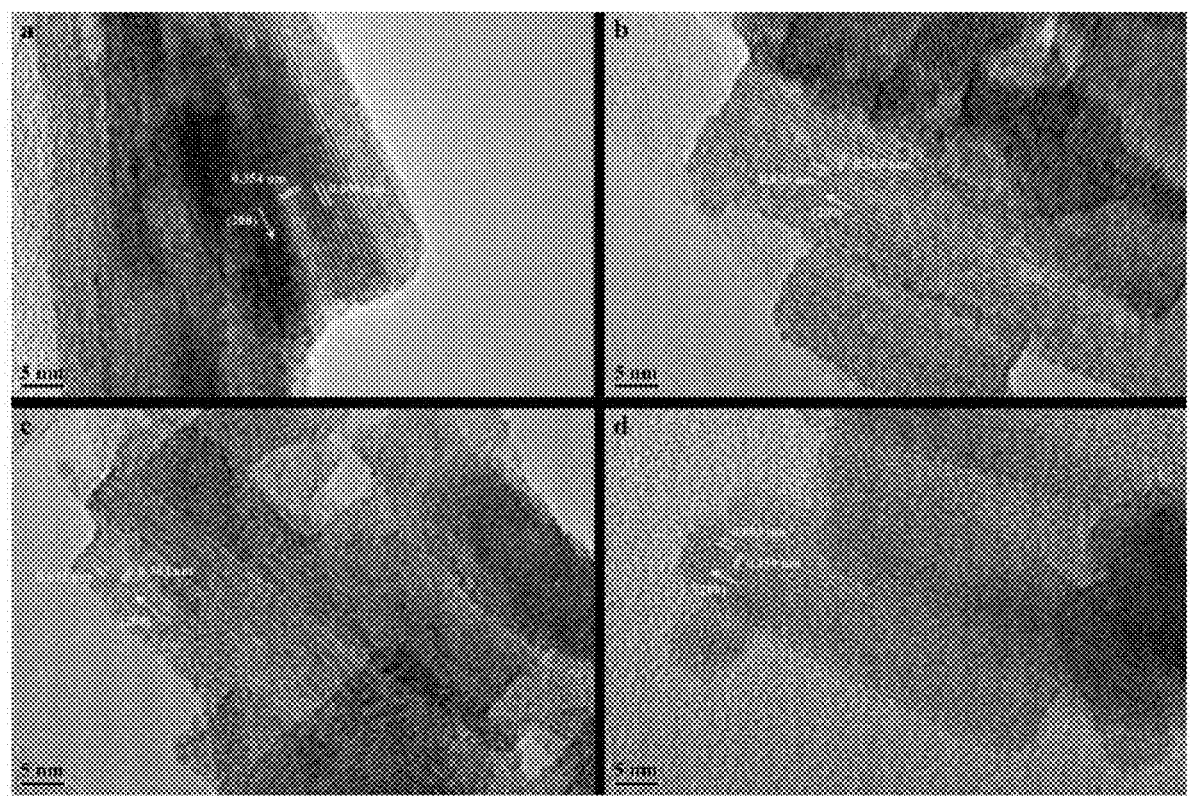
FIG. 19 shows HRTEM image of KWO lattice, samples grown at (a) 225, (b) 210, (c) 180, (d) 160° C.

TEM imaging was obtained using a JEOL JEM-2100 high-resolution analytical TEM. Samples were prepared on carbon grids by sonication. FIG. 18 shows that samples grown at higher temperature yielded longer nanorods. It can also be noted that a diameter of about 10 nm is standard among all samples indicating growth temperature does not affect the nanorods diameter. In FIG. 18, it can be seen that the nanorods start to become much longer on average than the other samples indicating a more efficient growth at higher temperatures. FIG. 19 presents the crystal lattice of KWO samples grown at 225, 210, 180, and 160° C. The lattice fringe spacing is summarized in Table 6. The measured lattice fringes do not vary much, which indicates the lattice spacing does not change with respect to growth temperature. This correlates well with the XRD spectra shown in FIG. 16. Overall, the basic crystal structure of the obtained material was not affected by growing temperature varying from 160 to 225° C.

TABLE 6

Lattice fringe spacing for samples grown at 160, 180, 210, and 225° C.

| Growth Temperature (° C.) | a-spacing (Å) | c-spacing (Å) |
|---|---|---|
| 160 | 6.038 | 3.598 |
| 180 | 6.320 | 3.636 |

TABLE 6-continued

Lattice fringe spacing for samples
grown at 160, 180, 210, and 225° C.

| Growth Temperature (° C.) | a-spacing (Å) | c-spacing (Å) |
|---|---|---|
| 210 | 6.356 | 3.634 |
| 225 | 6.388 | 3.542 |

Example 16: FT-IR Spectrum

Figure 20:
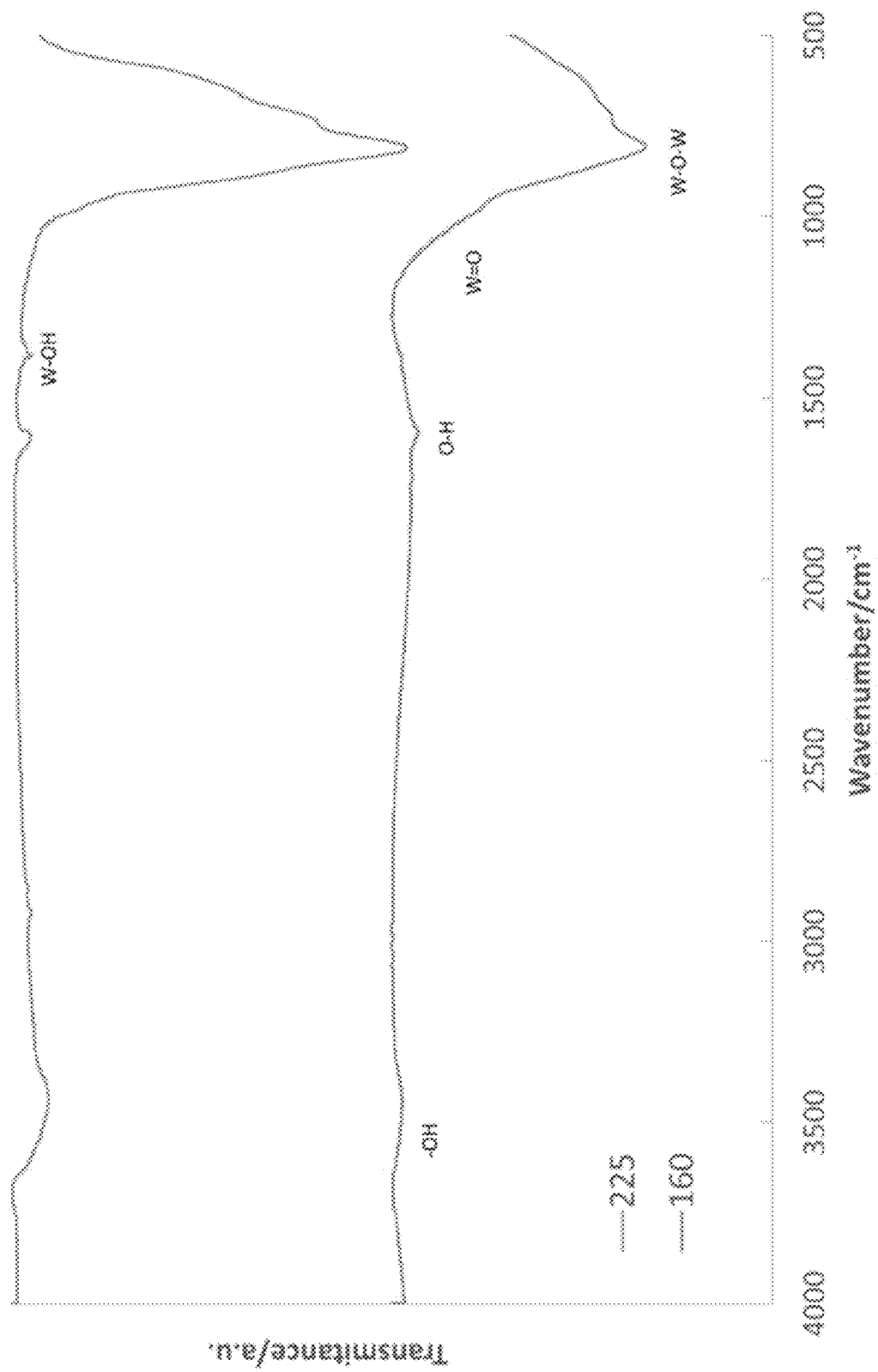
FIG. 20 shows FT-IR spectra of KWO grown at 160 and 225° C.

The FT-IR used in this study was a Thermo Scientific Nicolet 8700 FT-IR spectrometer. It was used to find if there was a change in the surface functionalization of the KWO samples grown at different temperatures. Further structural and functional groups of KWO grown at 160° C. and 225° C. were studied using FT-IR, see FIG. 20. It has been reported the $WO_3$ nanostructures can contain water within the crystal structure. [61, 62] This is confirmed in the results showing a wide band at $v=3,410$ $cm^{-1}$ and weak peak at $v=1,590$ $cm^{-1}$. These peaks can be attributed to —OH and $H_2O$ stretching vibration. A strong band at $v=806$ $cm^{-1}$ with shouldering at $v=716$ $cm^{-1}$ corresponds to O—W—O stretching vibration. This peak is stronger in the sample grown at 225° C., and this is likely due to the higher crystallinity which was presented earlier. Also, weak shouldering at $v=1,030$ $cm^{-1}$ can be attributed to the W=O vibrational mode. A weak peak at $v=1,380$ $cm^{-1}$ is attributed to W—OH. Interestingly, this peak only shows up for KWO synthesized at 225° C. indicating isolated hydroxyl groups only in this sample. From this data, KWO grown at higher temperatures presents —OH terminations while samples grown at lower temperatures do not. It has been shown that the —OH terminations can cause electrostatic interactions between the material and analyte. [63] The increased electrostatic interaction with acetone likely causes an improvement in sensing performance.

Example 17: Raman Spectroscopy

Figure 21:
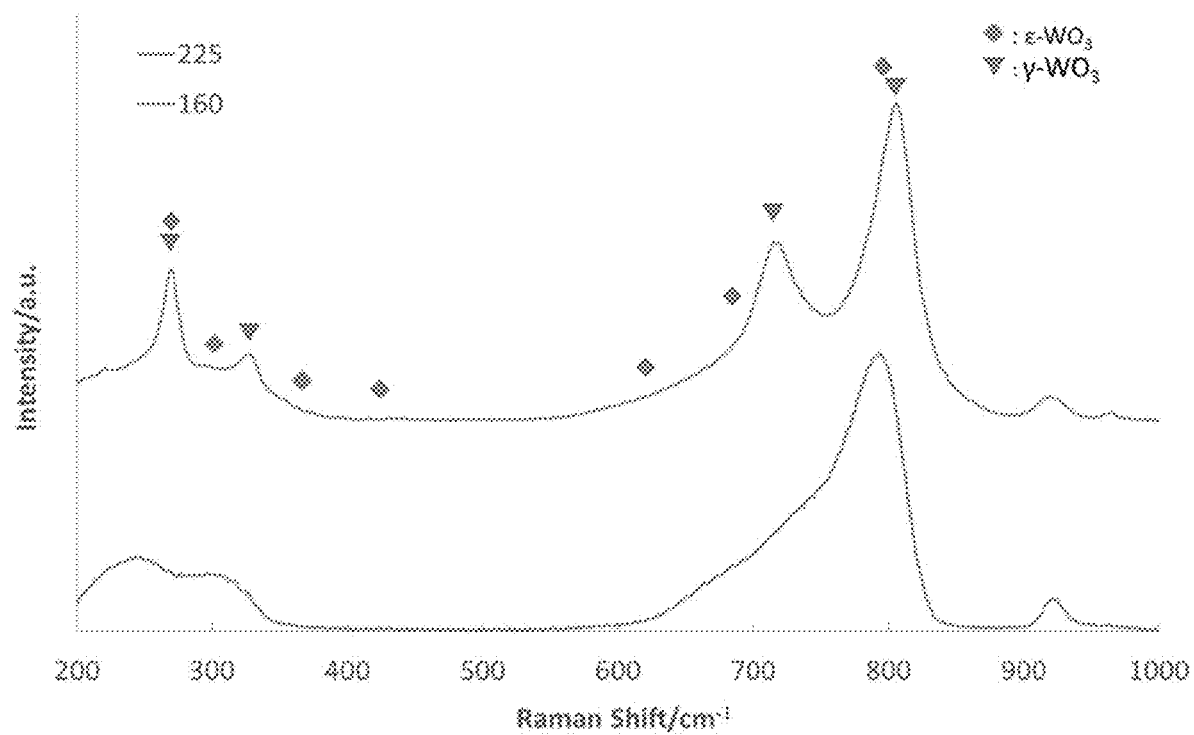
FIG. 21 shows Raman Spectra of KWO grown at 160° C. and 225° C.

Raman spectra were obtained using an Aramis Confocal Raman Imaging System with Horiba Jobin Yvon's Raman Spectrometer. It has been demonstrated previously that KWO has the ferroelectric property using a piezoresponse force microscope. [41] Raman spectroscopy was used to further study the ferroelectric property of KWO in this study. Previous reports have found that $WO_3$ exhibits this property in a bulk phase called ε-$WO_3$ which is only stable below −40° C. [24] However, it has also been found that ε-$WO_3$ can exist at room temperature as microcrystals in a bulk sample. [59] Raman has been utilized in other studies to better understand the effect that doping has on the crystal phase $WO_3$ expresses, and study the material's ferroelectric property. [27] Here, Raman spectroscopy was used to find peaks at room temperature, which can provide evidence of the existence of ε-$WO_3$ within the KWO crystal phase at room temperature. FIG. 21 shows the spectra obtained of KWO grown at 160 and 225° C. Both samples show peaks at $v=642$, and 688 $cm^{-1}$ which occur due to the presence of ε-$WO_3$. [60] These results confirm that the ε-$WO_3$ phase is present within the samples made. Factoring this in, the KWO grown at 225° C. shows further extended shoulder comparing to the sample grown at 160° C. indicating that KWO grown at higher temperature has a stronger ferroelectric property. This finding has shown us that the ferroelectric property has a large impact on KWO sensitivity to acetone, and has allowed us to improve KWO synthesis techniques for future study.

Example 18: Sensing Tests

Figure 22:
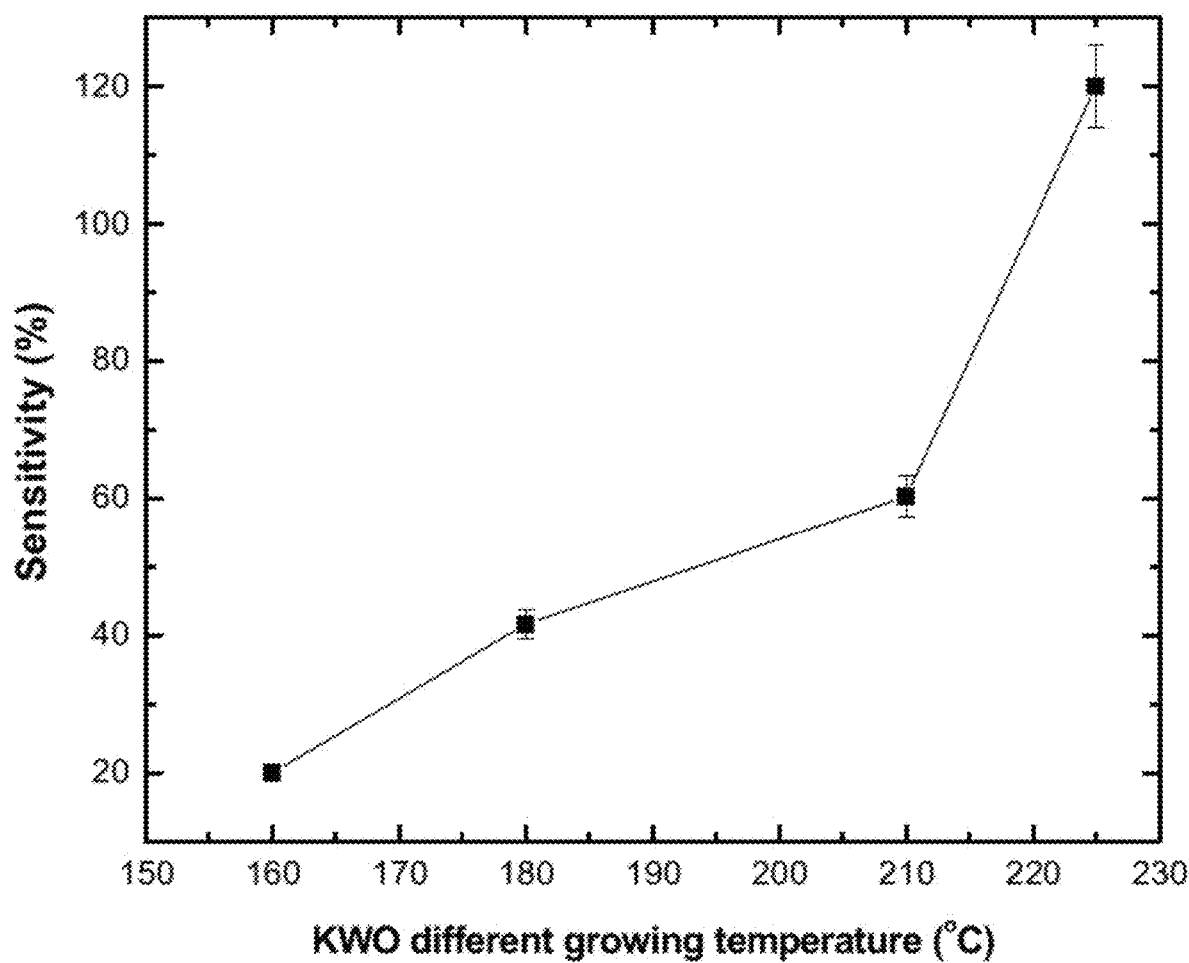
FIG. 22 shows sensitivity to acetone (50 ppm) using KWO grown at 160, 180, 210, and 225° C.

The acetone sensing performance has been done through a programmable chemiresistive gas sensor measurement system, which has been described elsewhere. [41, 54] Briefly, the acetone vapor is generated from OVG-4 (Owlstone, InC.) based on the theory of permeation tube. The concentration of acetone can be precisely controlled from 0 to 5 ppm. 50 ppm acetone is generated from acetone tank in dry nitrogen calibrated and made by Airgas, Inc. Once the acetone is exposure onto KWO film, a resistant change can be detected and recorded through an advanced circuit of signal collecting system. The sensing tests based on the as-synthesized KWO grown at different temperature to 50 ppm of acetone have been done and the results are shown in FIG. 22. Sensitivity to acetone was determined based on the typical equation for chemiresistive sensor, as shown below, to evaluate KWO sensing performance. In detail, it is calculated as the ratio between the change of resistance, $\Delta R=(R-R_o)$ and the baseline resistance, $R_o$ (measured without exposure of acetone) of the device.

$$[(R-R_o)/R_o]\times 100\% = \text{sensitivity.} \quad \text{Equation (1):}$$

Based on this equation, the sensitivity for KWO grown at 160, 180, 210, and 225° C. was calculated and shown in FIG. 22. The sensitivity increases as growth temperature increases. As long as the growing temperature is not too high to cause any phase transition this would be the general trend, but more study using equipment that can safely reach higher growing temperatures would be needed to see where that point is. Considering the results of XRD and HRTEM, in FIGS. 16 and 19 respectively, the results have shown that 225° C. KWO has higher crystallinity and longer nanorods. The sensing test results reveal that higher crystallinity and larger surface area can be one reason to result in better response of KWO to acetone. Also, an increased ferroelectric property, measured using Raman spectroscopy shown in FIG. 21, can be another important factor that results in the higher response of KWO to acetone. Due to the ferroelectric property being so important to the charge transfer between acetone and KWO, this indicates that improving this property is important to further improve KWO sensing performance to detect acetone. [27]

REFERENCES

Each of the following references is herein incorporated by reference in their entirety.

[1] International Diabetes Federation (IDF), Diabetes Atlas third Ed., Brussels, 2006.
[2] National Diabetes Statistics Report, 2017. Available: https://www.cdc.gov/diabetes/pdfs/data/statistics/national-diabetes-statistics-report.pdf.
[3] Y. Qiao, Z. Gao, Y. Liu, Y. Cheng, M. Yu, L. Zhao, Y. Duan, and Y. Liu. (2014, May). Breath Ketone Testing: A New Biomarker for Diagnosis and Therapeutic Monitoring of Diabetic Ketosis. *BioMed. Research International*, [Online], 2014(2014), pp. 1-5. Available: https://www.hindawi.com/journals/bmri/2014/869186/[4]
[4] Non-invasive substance concentration measurement using an optical bridge, by S. Harjunmaa, R. A. Peura, and J. A. Rolls (2002, Apr. 26). U.S. Pat. No. 7,003,337 B2.

[5] W. F. March, A. Muller, and P. Herbrechtsmeier, "Clinical trial of a noninvasive contact lens glucose sensor," *Diabetes Technology & Therapeutics,* 2004, pp. 782-789.

[6] A. E. Johannessen, B. Hinderling, C. Pugin, R. Mills, and G. Christiansen, "Injectable Osmotic Glucose Sensor and the Development of a Nanoporous Semi-permeable Membrane." *Diabetes Technology Meeting,* 2005, San Francisco: Diabetes Technology Society.

[7] H. T. Brown, M. N. Ediger, C. M. Fleming, E. L. Hull and M. Rohrscheib, "Clinical assessment of near infrared spectroscopy for noninvasive diabetes screening." *Diabetes Technology & Therapeutics,* 2005, pp. 456-466.

[8] R. Pandey, S. K. Paidi, T. A. Valdez, C. Zhang, N. Spegazzini, R. R. Dasari, and I. Barman. (2017, January). Noninvasive Measurements of Blood Glucose with Raman Spectroscopy. *Accounts of Chemical Research.* [Online] 50(2), pp. 2564-2'72, 2017. Available: http://pubs.acs.org/doi/ipdf/10.1021/acs.accounts.6b004726.

[9] C. Inc. (2002, August). Glucowatch G2: Automatic Glucose Biographer and Auto-sensors. Redwood City, Calif. [Online]. Available: https://www.accessdata.fda.gov/cdrh_docs/pdf/P990026S008b.pdf

[10] B. J. Novak, "Non-invasive monitoring of metabolism, diabetes and oxidative stress using exhaled human breath." Ph.D. dissertation, Dept. Chem., Univ. of California, Irvine, 2007.

[11] W. Miekisch, J. K. Schubert, and G. F. Noeldge-Schomburg. (2004, September). Diagnostic potential of breath analysis—focus on volatile organic compounds. *Clinica Chimica Acta.* [Online]. 347(1-2), pp. 25-39. Available: http://www.sciencedirect.com/science/article/pii/S0009898104002256

[12] A. Amann, P. Spanel, and D. Smith. (2007, February). Breath analysis: the approach towards clinical applications. *Mini-reviews in medicinal chemistry,* 7(2), pp. 115-129.

[13] M. Shirasu and K. Touhara. (2011, September). The scent of disease: volatile organic compounds of the human body related to disease and disorder. *Journal of biochemistry.* [Online]. 150(3), pp. 257-266. Available: https://academic.oup.com/jb/article/150/3/257/867730/The-scent-of-disease-volatile-organic-compounds-of

[14] G. Pennazza, M. Santonico, E. Martinelli, A. D'Amico, and C. Di Natale, "Interpretation of exhaled volatile organic compounds," *European respiratory monograph: exhaled biomarkers,* 49, ERS., UK, 2010, pp. 115-129.

[15] C. Wang, A. Mbi, and M. Shepherd. (2010, January). A study on breath acetone in diabetic patients using a cavity ringdown breath analyzer: Exploring correlations of breath actone with blood glucose and glycohemoglobinale. *IEEE Sensors Journal,* [Online], 10(1), pp. 54-63. Available: http://ieeexplore.ieee.org/stamp/stamp.jsp?arnumber=5350908

[16] C. Deng, J. Zhang, X. Yu, W. Zhang, and X. Zhang. (2004, October). Determination of acetone in human breath by gas chromatography-mass spectrometry and solid-phase microextraction with on-fiber derivatization. *Journal of Chromatography B,* [Online], 810(2), pp. 269-275. Available: http://www.sciencedirect.com/science/article/pii/S1570023204006579?via %3Dihub

[17] M. Yoshimura and K. Byrappa. (2008, April). Hydrothermal processing of materials: past, present and future. *J. Mater. Sci.,* [Online] 43(7), pp. 2085-2103. Available: https://link.springer.com/article/10.1007/s10853-007-1853-x

[18] J. Jitputti, S. Pavasupree, Y. Suzuki, and S. Yoshikawa. (2008, January). Synthesis of $TiO_2$ nanotubes and its photocatalytic activity for $H_2$ evolution. *Japanese Journal of Applied Physics,* [Online], 47(1), pp. 751-756. Available: http://iopscience.iop.org/article/10.1143/JJAP.47.751/pdf

[19] S. Supothina, M. Suwan, and A. Wisitsoraat. (2014, August). Hydrothermal synthesis of $K_2W_4O_{13}$ nanowire with high $H_2S$ gas sensivitity. *Microelectronic Engineering.* [Online]. 126, pp. 88-92. Available: http://www.sciencedirect.com/science/article/pii/S0167931714002676

[20] D. Wang and Q. Zhang, "Room temperature acetone sensor based on nanostructured $K_2W_7O_{22}$." *Sensors,* 2016 IEEE, 2016, [Online], pp. 1-3. Available: http://ieeexplore.ieee.org/document/7808635/[21]

MR. Hossain, Q. Zhang, M. Johnson, and D. Wang. (2017, October). Investigation of humidity cross-interference effect on acetone breath sensor based on nanostructured $K_2W_7O_{22}$. Engineering Press, [Online], 1(1), pp. 30-34. Available: http://onlinepublishingpress.com/engineering-press/article-in-press.php

[22] C. H. Deng, J. Zhang, X. F. Yu, W. Zhang, and X. M. Zhang. (2004, October). Determination of acetone in human breath by gas chromatography-mass spectrometry and solid-phase microextraction with on-fiber derivatization. *Journal of Chromatography B,* [Online], 810(2), pp:269-275. Available: http://www.sciencedirect.com/science/article/pii/S1570023204006579

[23] M. X. Sun, Z. Y. Chen, Z. Y. Gong, X. M. Zhao, C. Y. Jiang, Y. Yuan, Z. Wang, Yi. Li, and C. Wang. (2015, February). Determination of breath acetone in 149 Type 2 diabetic patients using a ringdown breath-acetone analyzer. *Analytical and Bioanalytical Chemistry,* [Online] 407(6), pp. 1641-1650. Available: https://link.springer.com/article/10.1007%2Fs00216-014-8401-8

[24] M. Righettoni, A. Tricoli, and S. E. Pratsinis. (2010, May). Si:$WO_3$ Sensors for Highly Selective Detection of Acetone for Easy Diagnosis of Diabetes by Breath Analysis. *Analytical Chemistry,* [Online], 82(9), pp. 3581-3587. Available: http://pubs.acs.org/doi/pdf/10.1021/ac902695n

[25] M. Righettoni, A. Tricoli, S. Gass, A. Schmid, A. Amann, and S. E. Pratsinis. (2012, August). Breath acetone monitoring by portable Si:$WO_3$ gas sensors. *Analytica chimica acta,* [Online], 738, pp. 69-75. Available: http://www.sciencedirect.com/science/article/pii/S0003267012008276?via %3Dihub

[26] K. W. Kao, M. C. Hsu, Y. H. Chang, S. Gwo, and J. A. Yeh. (2012, May). A Sub-ppm Acetone Gas Sensor for Diabetes Detection Using 10 nm Thick Ultrathin InN FETs. *Sensors,* [Online], 12(6), pp. 7157-7168. Available: http://www.mdpi.com/1424-8220/12/6/7157/htm

[27] L. Wang, A. Teleki, S. E. Pratsinis, and P. I. Gouma. (2008, July). Ferroelectric $WO_3$ nanoparticles for acetone selective detection. *Chemistry of Materials,* [Online], 20(15), pp. 4794-4796. Available: http://pubs.acs.org/doi/pdfplus/10.1021/cm800761e

[28] L. Wang, K. Kalyanasundaram, M. Stanacevic, and P. Gouma. (2010, October). Nanosensor Device for Breath Acetone Detection. *Sensor Letters,* [Online]. 8(1-4), pp. 709-712. Available: http://www.ece.sunysb.edu/~milutin/pubs/journal/gasSensorSL10.pdf

[29] A. Vomiero, S. Bianchi, E. Comini, G. Faglia, M. Ferroni, and G. Sberveglieri. (2007, December). Controlled growth and sensing properties of $In_2O_3$ nanowires. *Crystal Growth & Design.* [Online]. 7(12), pp. 2500-2504. Available: http://pubs.acs.org/doi/pdf/10.1021/cg070209p

[30] N. Kakati, S. H. Jee, S. H. Kim, J. Y. Oh, and Y. S. Yoon. (2010, October). Thickness dependency of sol-gel derived ZnO thin films on gas sensing behaviors. *Thin Solid Films*, [Online], 519(1), pp. 494-498. Available: http://www.sciencedirect.com/science/article/pii/S0040609010011193

[31] P. A. Murade, V. S. Sangawar, G. N. Chaudhari, V. D. Kapse, and A. U. Bajpeyee. (2011, May). Acetone gas-sensing performance of Sr-doped nanostructured $LaFeO_3$ semiconductor prepared by citrate sol-gel route. *Current Applied Physics*, [Online], 11(3), pp. 451-456. Available: http://www.sciencedirect.com/science/article/pii/S1567173910002749

[32] A. Teleki, S. E. Pratsinis, K. Kalyanasundaram, and P. I. Gouma. (2006, December). Sensing of organic vapors by flame-made $TiO_2$ nanoparticles. *Sensors and Actuators B—Chemical*, [Online], 119(2), pp. 683-690. Available: http://www.sciencedirect.com/science/article/pii/S0925400506000475

[33] F. Qu, J. Liu, Y. Wang, S. Wen, Y. Chen, X. Li, and S. Ruan. (2014, August). Hierarchical $Fe_3O_4@Co_3O_4$ core-shell microspheres: Preparation and acetone sensing properties. *Sensors and Actuators B—Chemical*, [Online], 199, pp. 346-353. Available: http://www.sciencedirect.com/science/article/pii/S0925400514004031

[34] H. Ahn, Y. Wang, S. H. Jee, M. Park, Y. S. Yoon, and D.-J. Kim. (2011, August). Enhanced UV activation of electrochemically doped Ni in ZnO nanorods for room temperature acetone sensing. *Chemical Physics Letters*, [Online], 511(4-6), pp. 331-335. Available: http://www-.sciencedirect.com/science/article/pii/S000926141100755X

[35] Artur Rydosz, A Negative Correlation Between Blood Glucose and Acetone Measured in Healthy and Type 1 Diabetes Mellitus Patient Breath, J Diabetes Sci Technol 2015, 9, 881-884, doi: 10.1177/1932296815572366

[36] H. Jamalabadi and N. Alizadeh, *IEEE Sens.* 1, 2017, 17, 2322-2328

[37] K. W. Kao, M. C. Hsu, Y. H. Chang, S. Gwo and J. A. Yeh, Sensors, 2012, 12, 7157-7168.

[38] A. Hazra, B. Bhowmik, K. Dutta and P. Bhattacharyya. Presented in Seventh International Conference on Sensing Technology (ICST), IEEE, Wellington, New Zealand, 3-5 Dec. 2013.

[39] D. Subhashis, A. Bag, R. Kumar and D. Biswas, *IEEE-EDL*, 2017, 38, 383-386

[40] Chemiresistors, http://www.sandia.gov/mstc/_assets/documents/Fact_Sheets/sensors/2chemiresistor.pdf, (accessed 7 Apr. 2018)

[41] D. Wang, Q. Zhang, M. R. Hossain and M. Johnson, IEEE Sens. J., 2018, 18, 4399-4404.

[42] N. Barsan and U. Weimar, *J. of Electroc.*, 2001, 7, 143-167

[43] Dipole moment, https://en.wikipedia.org/wiki/Dipole_moment (3Apr. 2018)

[44] B. Caveman (2014, March). *Ketonix Review*. [Online]. Available: bjjcaveman.com/2014/03/15/ketonix-review/[45]

[45] T. Soper (2013, November). This handheld device helps you lose weight by detecting acetone levels in your breath. [Online]. Available: www.geekwire.com/2013/small-device-detects-acetone-levels-breath-measure-fat-burning/[46]

[46] C. A. Newton, P. Raskin, *Arch Intern Med.*, 2004, 164: 1925-1931.

[47] J. C. Anderson. Obesity, 2015, 23: 2327-2334.

[48] L. C. McGuire, A. M Cruickshank, P. T. Munro, Emerg. Med. J. 2006, 23: 417-420.

[49] Electrostatic Interactions. Available online: https://www.sciencedirect.com/topics/chemistry/electrostaticinteractions (accessed on 1 Sep. 2018).

[50] Fine, G. F.; Cavanagh, L. M.; Afonja, A.; Binions, R. Metal Oxide Semi-Conductor Gas Sensors in Environmental Monitoring. Sensors 2010, 10, 5469-5502. [CrossRef] [PubMed].

[51] Chemical Sensors. Available online: https://www.nap.edu/read/4782/chapter/10#74 (accessed on 15 Oct. 2018).

[52] Sensor. Available online: https://en.wikipedia.org/wiki/Sensor (accessed on 15 Oct. 2018).

[53] Kargar, A. Sensitivity Analysis of Silicon Nanowire Chemical Sensor. In Proceedings of the 8th IEEE Conference on Nanotechnology, Arlington, Tex., USA, 18-21 Aug. 2008.

[54] MR Hossain, Q Zhang, M Johnson, D Wang (2018) Highly Sensitive Room-Temperature Sensor Based on Nanostructured $K_2W_7O_{22}$ for Application in the Non-Invasive Diagnosis of Diabetes. Sensors 18(11): 3703-3712.

[55] Buszewski, B., Kesy, M., Ligor, T., & Amann, A. (2007). Human exhaled air analytics: Biomarkers of diseases. Biomedical Chromatography, 21(6), 553-566. doi: 10.1002/bmc.835.

[56] Konvalina, G., & Haick, H. (2014). Sensors for Breath Testing: From Nanomaterials to Comprehensive Disease Detection. Accounts of Chemical Research, 47(1), 66-76. doi:10.1021/ar400070m.

[57] Jia, Q. Q., Ji, H. M., Wang, D. H., Bai, X., Sun, X. H., & Jin, Z. G. (2014). Exposed facets induced enhanced acetone selective sensing property of nanostructured tungsten oxide. Journal of Materials Chemistry A, 2(33), 13602-13611. doi:10.1039/c4ta01930j.

[58] Tang, B. L., Jiang, G. H., Chen, W. X., & Wan, J. M. (2015). First-Principles Study on Hexagonal $WO_3$ for HCHO Gas Sensing Application. Acta Metallurgica Sinica-English Letters, 28(6), 772-780. doi:10.1007/s40195-015-0260-6.

[59] Woodward, P. M., Sleight, A. W., & Vogt, T. (1997). Ferroelectric tungsten trioxide. Journal of Solid State Chemistry, 131(1), 9-17. doi:10.1006/jssc.1997.7268.

[60] Arai, M., Hayashi, S., Yamamoto, K., & Kim, S. S. (1990). RAMAN STUDIES OF PHASE-TRANSITIONS IN GAS-EVAPORATED $WO_3$ MICROCRYSTALS. Solid State Communications, 75(7), 613-616. doi: 10.1016/0038-1098(90)90429-f.

[61] Lopes, L. F., Pontes, F. M., Garcia, L. O., Pontes, D. S. L., Padovani, D., Chiquito, A. J., Longo, E. (2018). Silver-controlled evolution of morphological, structural, and optical properties of three dimensional hierarchical $WO_3$ structures synthesized from hydrothermal method. Journal of Alloys and Compounds, 736, 143-151. doi: 10.1016/j.jallcom.2017.11.095.

[62] Li, T. T., Shen, Y. B., Zhao, S. K., Chen, X. X., Li, G. D., Lu, R., Shen, Y. S. (2018).
Xanthate sensing properties of Pt-functionalized $WO_3$ microspheres synthesized by one-pot hydrothermal method. Ceramics International, 44(5), 4814-4823. doi: 10.1016/j.ceramint.2017.12.069.

[63] Mu, W. J., Li, M., Li, X. L., Ma, Z. P., Zhang, R., Yu, Q. H., . . . Jian, Y. (2015). Guanidine sulfate assisted synthesis of hexagonal $WO_3$ nanoparticles with enhanced adsorption properties. Dalton Transactions, 44(16), 7419-7427. doi:10.1039/c5dt00103j.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A device for detecting Volatile Organic Compounds (VOCs) at room temperature and below 100° C., comprising:
 (a) a VOC sensor comprised of
  (i) a pair of electrodes,
  (ii) a moisture sensor, and
  (iii) nanostructured $K_2W_7O_{22}$ extending between the pair of electrodes;
 (b) a pressure sensor; and
 (c) a microprocessor operably connected to the VOC sensor and configured to calculate a concentration of a VOC based, at least in part, on a resistance change of the nanostructured $K_2W_7O_{22}$ caused by adsorption of the VOC to the nanostructured $K_2W_7O_{22}$.

2. The device of claim 1 wherein the VOC sensor is an acetone sensor.

3. The device of claim 1, wherein the device further includes an electric fan.

4. The device of claim 1, wherein the device further includes a desiccant placed within or connected to the device.

5. The device of claim 2, wherein the device further includes an electric fan.

6. The device of claim 2, wherein the device further includes a desiccant placed within or connected to the device.

7. A method of diagnosing a subject as in a state of ketosis comprising:
 (a) having a subject breathe into a device according to claim 1, to determine an acetone concentration; and
 (b) diagnosing the subject as in a state of ketosis if the acetone concentration is greater than or equal to 1.7 ppm acetone.

8. The method of claim 7, wherein the state of ketosis is selected from ketogenic diet, lung cancer, alcoholism, alcoholic binge drinking, diabetes, fasting, weight loss, or combinations thereof.

9. The method of claim 8, wherein the state of ketosis is diabetes.

10. The method of claim 7, wherein the method is performed at ambient temperature.

11. The method of claim 10 and further comprising administering treatment to the diagnosed subject.

12. A method of detecting VOCs in the breath of a subject comprising:
 (a) having a subject breathe into a device according to claim 1; and
 (b) computing the ppm of the VOC in the subject's breath.

* * * * *